(12) United States Patent
Putnam et al.

(10) Patent No.: US 11,633,661 B2
(45) Date of Patent: *Apr. 25, 2023

(54) VIDEO REBROADCASTING WITH MULTIPLEXED COMMUNICATIONS AND DISPLAY VIA SMART MIRRORS, AND SMART WEIGHT INTEGRATION

(71) Applicant: Curiouser Products Inc., New York, NY (US)

(72) Inventors: Brynn Putnam, New York, NY (US); Kristie D'Ambrosio-Correll, Sands Point, NY (US)

(73) Assignee: Curiouser Products Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,255

(22) Filed: Apr. 25, 2022

(65) Prior Publication Data

US 2022/0249908 A1 Aug. 11, 2022

Related U.S. Application Data

(63) Continuation of application No. 17/315,558, filed on May 10, 2021, now Pat. No. 11,351,439.

(Continued)

(51) Int. Cl.
*A63B 71/06* (2006.01)
*A63B 24/00* (2006.01)
(Continued)

(52) U.S. Cl.
CPC .......... *A63B 71/0622* (2013.01); *A47G 1/02* (2013.01); *A63B 24/0006* (2013.01);
(Continued)

(58) Field of Classification Search
None
See application file for complete search history.

(56) References Cited

U.S. PATENT DOCUMENTS 5,681,223 A 10/1997 Weinreich
6,059,692 A 5/2000 Hickman
(Continued)

FOREIGN PATENT DOCUMENTS

CN 102413886 A 4/2012
CN 203311128 U 11/2013
(Continued)

OTHER PUBLICATIONS

International Search Report and Written Opinion dated Oct. 9, 2019 for International Application No. PCT/US2019/034292, 18 pages.
(Continued)

*Primary Examiner* — Jwalant Amin
(74) *Attorney, Agent, or Firm* — Cooley LLP

(57) ABSTRACT

A method includes causing display, during a first time period and via a first set of multiple smart mirrors, of live video depicting at least one user associated with the first set of multiple smart mirrors, without displaying a workout video. The method also includes causing display, during a second time period following and mutually exclusive of the first time period, and via a second set of multiple smart mirrors, of a workout video and a representation of at least one user associated with the second set of smart mirrors. The method also includes causing display, during a third time period following and mutually exclusive of the second time period, and via a third set of multiple smart mirrors, of live video depicting at least one user associated with the third set of multiple smart mirrors.

20 Claims, 15 Drawing Sheets

Related U.S. Application Data

(60) Provisional application No. 63/144,047, filed on Feb. 1, 2021, provisional application No. 63/074,894, filed on Sep. 4, 2020.

(51) Int. Cl.

| | |
|---|---|
| *G06V 40/20* | (2022.01) |
| *G06V 40/10* | (2022.01) |
| *A47G 1/02* | (2006.01) |
| *G06F 3/01* | (2006.01) |
| *G06T 19/00* | (2011.01) |

(52) U.S. Cl.
CPC .......... *A63B 24/0062* (2013.01); *G06F 3/011* (2013.01); *G06T 19/006* (2013.01); *G06V 40/103* (2022.01); *G06V 40/23* (2022.01); *A63B 2024/0009* (2013.01); *A63B 2024/0065* (2013.01); *A63B 2071/063* (2013.01); *A63B 2071/0638* (2013.01); *A63B 2220/12* (2013.01); *A63B 2220/40* (2013.01); *A63B 2220/75* (2013.01); *A63B 2220/805* (2013.01); *A63B 2225/12* (2013.01); *A63B 2230/06* (2013.01); *A63B 2230/50* (2013.01)

(56) References Cited

U.S. PATENT DOCUMENTS

| | | |
|---|---|---|
| 6,921,351 B1 | 7/2005 | Hickman et al. |
| 7,010,508 B1 | 3/2006 | Lockwood |
| 7,020,888 B2 | 3/2006 | Reynolds et al. |
| 7,055,169 B2 | 5/2006 | Delpuch et al. |
| 7,152,470 B2 | 12/2006 | Impioe et al. |
| 7,206,250 B2 | 4/2007 | Groux |
| 7,455,412 B2 | 11/2008 | Rottcher |
| 7,589,893 B2 | 9/2009 | Rottcher |
| 7,631,338 B2 | 12/2009 | Del Sesto et al. |
| 7,699,753 B2 | 4/2010 | Daikeler et al. |
| 7,725,740 B2 | 5/2010 | Kudelski et al. |
| 7,931,604 B2 | 4/2011 | Even et al. |
| 7,946,961 B2 | 5/2011 | Blum et al. |
| 8,081,158 B2 | 12/2011 | Harris |
| 8,311,474 B2 | 11/2012 | McAvoy et al. |
| 8,496,563 B2 | 7/2013 | Komatsu et al. |
| 8,519,938 B2 | 8/2013 | Hernandez et al. |
| 8,620,413 B2 | 12/2013 | Prstojevich et al. |
| 8,821,350 B2 | 9/2014 | Maertz |
| 8,882,641 B2 | 11/2014 | Cutler et al. |
| 8,912,909 B2 | 12/2014 | Al-All et al. |
| 8,951,168 B2 | 2/2015 | Baudhuin |
| 9,011,293 B2 | 4/2015 | Shavit et al. |
| D728,710 S | 5/2015 | Koduri et al. |
| 9,037,530 B2 | 5/2015 | Tan et al. |
| 9,122,320 B1 | 9/2015 | Rowles et al. |
| 9,174,085 B2 | 11/2015 | Foley et al. |
| 9,233,276 B1 | 1/2016 | Foley et al. |
| 9,259,615 B2 | 2/2016 | Weast et al. |
| 9,278,256 B2 | 3/2016 | Tchao et al. |
| 9,292,935 B2 | 3/2016 | Koduri et al. |
| 9,330,239 B2 | 5/2016 | Koduri et al. |
| 9,364,714 B2 | 6/2016 | Koduri et al. |
| 9,406,336 B2 | 8/2016 | Bose et al. |
| 9,609,261 B2 | 3/2017 | Yamada et al. |
| 9,712,581 B2 | 7/2017 | Tinsman |
| 9,842,508 B2 | 12/2017 | Crabtree |
| 9,861,855 B2 | 1/2018 | Foley et al. |
| 9,975,002 B2 | 5/2018 | Pinkerton |
| 10,021,188 B2 | 7/2018 | Oleson et al. |
| 10,022,590 B2 | 7/2018 | Foley et al. |
| 10,068,257 B1 | 9/2018 | Mosthaf |
| 10,109,216 B2 | 10/2018 | Lagree et al. |
| 10,143,405 B2 | 12/2018 | Jayalath et al. |
| 10,188,930 B2 | 1/2019 | Winsper et al. |
| 10,232,220 B2 | 1/2019 | Winsper et al. |
| 10,322,315 B2 | 6/2019 | Foley et al. |
| 10,375,429 B1 | 8/2019 | Greenfield |
| 10,413,250 B2 | 9/2019 | Leboeuf et al. |
| 10,467,926 B2 | 11/2019 | Ghaffari et al. |
| 10,486,026 B2 | 11/2019 | Foley et al. |
| 10,575,759 B2 | 3/2020 | Salamatian et al. |
| 10,639,521 B2 | 5/2020 | Foley et al. |
| 10,692,407 B2 | 6/2020 | Dunn et al. |
| 10,702,760 B2 | 7/2020 | Lagree et al. |
| 10,716,969 B2 | 7/2020 | Hoang |
| 10,744,371 B2 | 8/2020 | Mohrman et al. |
| 10,758,780 B2 | 9/2020 | Putnam |
| 10,828,551 B2 | 11/2020 | Putnam |
| 10,898,760 B2 | 1/2021 | Packles et al. |
| 10,923,225 B2 | 2/2021 | Riley et al. |
| 10,960,266 B2 | 3/2021 | Messinger |
| 10,981,047 B2 | 4/2021 | Putnam |
| 11,045,709 B2 | 6/2021 | Putnam |
| 11,065,527 B2 | 7/2021 | Putnam |
| 11,081,224 B2 | 8/2021 | Foley et al. |
| 11,090,547 B2 | 8/2021 | Putnam |
| 11,110,336 B2 | 9/2021 | Putnam |
| 11,117,038 B2 | 9/2021 | Putnam |
| 11,117,039 B2 | 9/2021 | Putnam |
| 11,123,626 B1 | 9/2021 | Putnam |
| 11,135,503 B2 | 10/2021 | Putnam |
| 11,135,504 B1 | 10/2021 | Putnam |
| 11,135,505 B2 | 10/2021 | Putnam |
| 11,167,172 B1 | 11/2021 | Putnam |
| 11,173,377 B1 | 11/2021 | Putnam |
| 11,173,378 B2 | 11/2021 | Putnam |
| 11,179,620 B2 | 11/2021 | Putnam |
| 11,219,816 B2 | 1/2022 | Putnam |
| 11,253,770 B2 | 2/2022 | Putnam |
| 11,298,606 B2 | 4/2022 | Putnam |
| 11,351,439 B2 | 6/2022 | Putnam et al. |
| 11,376,484 B2 | 7/2022 | Putnam |
| 11,383,146 B1 | 7/2022 | Putnam |
| 11,383,147 B2 | 7/2022 | Putnam |
| 11,383,148 B2 | 7/2022 | Putnam |
| 11,400,357 B2 | 8/2022 | Putnam |
| 11,433,275 B2 | 9/2022 | Putnam |
| 11,465,030 B2 | 10/2022 | Putnam et al. |
| 2002/0080494 A1 | 6/2002 | Meine |
| 2005/0063566 A1 | 3/2005 | van Beek et al. |
| 2005/0192156 A1 | 9/2005 | Daikeler et al. |
| 2006/0184427 A1 | 8/2006 | Singh |
| 2007/0069977 A1 | 3/2007 | Adderton |
| 2007/0219057 A1 | 9/2007 | Fleishman |
| 2007/0219059 A1 | 9/2007 | Schwartz et al. |
| 2008/0146887 A1 | 6/2008 | Rao et al. |
| 2008/0204327 A1 | 8/2008 | Lee et al. |
| 2008/0207401 A1 | 8/2008 | Harding |
| 2008/0303949 A1 | 12/2008 | Ciudad et al. |
| 2009/0291726 A1 | 11/2009 | Svensson |
| 2009/0291805 A1 | 11/2009 | Blum et al. |
| 2009/0298650 A1 | 12/2009 | Kutliroff |
| 2010/0022351 A1 | 1/2010 | Lanfermann et al. |
| 2010/0214662 A1 | 8/2010 | Takayanagi et al. |
| 2010/0323846 A1 | 12/2010 | Komatsu et al. |
| 2011/0056102 A1 | 3/2011 | Reid et al. |
| 2011/0154258 A1 | 6/2011 | Hope et al. |
| 2011/0172064 A1 | 7/2011 | Cutler et al. |
| 2011/0224999 A1 | 9/2011 | Baccarella-Garcia et al. |
| 2011/0267488 A1 | 11/2011 | Matsuura et al. |
| 2011/0275940 A1 | 11/2011 | Nims et al. |
| 2012/0069131 A1 | 3/2012 | Abelow |
| 2012/0206577 A1 | 8/2012 | Guckenberger et al. |
| 2012/0212484 A1 | 8/2012 | Haddick et al. |
| 2012/0289850 A1 | 11/2012 | Xu et al. |
| 2013/0141607 A1 | 6/2013 | Anabuki |
| 2013/0171601 A1 | 7/2013 | Yuasa et al. |
| 2013/0286047 A1 | 10/2013 | Katano et al. |
| 2014/0038781 A1 | 2/2014 | Foley et al. |
| 2014/0135173 A1 | 5/2014 | Watterson |
| 2014/0209400 A1 | 7/2014 | Yao et al. |
| 2014/0228985 A1 | 8/2014 | Elliott et al. |
| 2015/0003621 A1 | 1/2015 | Trammell |
| 2015/0038806 A1 | 2/2015 | Kaleal et al. |
| 2015/0061891 A1 | 3/2015 | Oleson et al. |

(56) References Cited

U.S. PATENT DOCUMENTS

| | | |
|---|---|---|
| 2015/0082408 A1 | 3/2015 | Yeh et al. |
| 2015/0134773 A1 | 5/2015 | Salem |
| 2015/0146778 A1 | 5/2015 | de Cicco et al. |
| 2015/0157938 A1 | 6/2015 | Domansky et al. |
| 2015/0182798 A1 | 7/2015 | Carriveau et al. |
| 2015/0339854 A1 | 11/2015 | Adler et al. |
| 2015/0348429 A1 | 12/2015 | Dalal et al. |
| 2016/0027259 A1 | 1/2016 | Jeffries |
| 2016/0089574 A1 | 3/2016 | Henning et al. |
| 2016/0121165 A1 | 5/2016 | Foley et al. |
| 2016/0193502 A1 | 7/2016 | Kim et al. |
| 2016/0220808 A1 | 8/2016 | Hyde et al. |
| 2016/0240100 A1 | 8/2016 | Rauhala et al. |
| 2016/0321932 A1 | 11/2016 | Mitchell et al. |
| 2017/0188087 A1 | 6/2017 | Kyoun et al. |
| 2017/0189752 A1 | 7/2017 | Mohrman et al. |
| 2017/0199576 A1 | 7/2017 | Schmitz-Le Hanne |
| 2017/0296874 A1 | 10/2017 | Zamir et al. |
| 2017/0319906 A1 | 11/2017 | Chang et al. |
| 2018/0028896 A1 | 2/2018 | Ray |
| 2018/0056132 A1 | 3/2018 | Foley et al. |
| 2018/0126223 A1 | 5/2018 | Foley et al. |
| 2018/0126248 A1 | 5/2018 | Dion et al. |
| 2018/0126249 A1 | 5/2018 | Consiglio et al. |
| 2018/0140903 A1 | 5/2018 | Poure et al. |
| 2018/0268747 A1 | 9/2018 | Braun |
| 2018/0271409 A1 | 9/2018 | Gong et al. |
| 2018/0304118 A1 | 10/2018 | French |
| 2018/0318647 A1 | 11/2018 | Foley et al. |
| 2018/0339195 A1 | 11/2018 | Bernotas |
| 2018/0369642 A1 | 12/2018 | Chang et al. |
| 2019/0021616 A1 | 1/2019 | Day et al. |
| 2019/0022388 A1 | 1/2019 | Stucke |
| 2019/0111318 A1 | 4/2019 | Evancha et al. |
| 2019/0126099 A1 | 5/2019 | Hoang |
| 2019/0163431 A1 | 5/2019 | Rodriguez et al. |
| 2019/0184234 A1 | 6/2019 | Packles et al. |
| 2019/0209777 A1 | 7/2019 | O'Connell et al. |
| 2019/0290965 A1 | 9/2019 | Oren |
| 2019/0320140 A1 | 10/2019 | Lyu |
| 2019/0336827 A1 | 11/2019 | Intonato et al. |
| 2019/0340554 A1 | 11/2019 | Dotan-Cohen et al. |
| 2020/0014967 A1 | 1/2020 | Putnam |
| 2020/0016457 A1 | 1/2020 | Ben-Chanoch et al. |
| 2020/0047030 A1 | 2/2020 | Ward et al. |
| 2020/0054931 A1 | 2/2020 | Martin et al. |
| 2020/0114203 A1 | 4/2020 | DeLuca |
| 2020/0160961 A1 | 5/2020 | Wadhawan et al. |
| 2020/0261770 A1 | 8/2020 | Foley et al. |
| 2020/0359147 A1 | 11/2020 | Reilly et al. |
| 2020/0406119 A1 | 12/2020 | Woltermann |
| 2021/0008413 A1 | 1/2021 | Asikainen et al. |
| 2021/0138332 A1 | 5/2021 | Dalebout et al. |
| 2021/0146197 A1 | 5/2021 | Packles et al. |
| 2021/0150773 A1 | 5/2021 | Muendel et al. |
| 2021/0236874 A1 | 8/2021 | Ward et al. |
| 2021/0252369 A1 | 8/2021 | Devine et al. |
| 2021/0303058 A1 | 9/2021 | Hsieh et al. |
| 2021/0326010 A1 | 10/2021 | Kaemmerer et al. |
| 2021/0339110 A1 | 11/2021 | Putnam |
| 2021/0342952 A1 | 11/2021 | Putnam |
| 2021/0362031 A1 | 11/2021 | Putnam |
| 2021/0370154 A1 | 12/2021 | Putnam |
| 2021/0379471 A1 | 12/2021 | Putnam |
| 2021/0379472 A1 | 12/2021 | Putnam |
| 2021/0379473 A1 | 12/2021 | Putnam |
| 2021/0397390 A1 | 12/2021 | Li et al. |
| 2021/0405950 A1 | 12/2021 | Li et al. |
| 2022/0023738 A1 | 1/2022 | Putnam |
| 2022/0032162 A1 | 2/2022 | Putnam |
| 2022/0032163 A1 | 2/2022 | Putnam |
| 2022/0050655 A1 | 2/2022 | Chiang et al. |
| 2022/0072375 A1 | 3/2022 | Putnam et al. |
| 2022/0072376 A1 | 3/2022 | Putnam et al. |
| 2022/0072379 A1 | 3/2022 | Putnam et al. |
| 2022/0078503 A1 | 3/2022 | Putnam et al. |
| 2022/0105417 A1 | 4/2022 | Putnam |
| 2022/0193526 A1 | 6/2022 | Putnam |
| 2022/0203205 A1 | 6/2022 | Putnam |
| 2022/0241647 A1 | 8/2022 | Putnam et al. |
| 2022/0249908 A1 | 8/2022 | Putnam et al. |
| 2022/0339521 A1 | 10/2022 | Putnam |
| 2022/0339522 A1 | 10/2022 | Putnam |

FOREIGN PATENT DOCUMENTS

| | | |
|---|---|---|
| CN | 104144201 A | 11/2014 |
| CN | 106055082 A | 10/2016 |
| CN | 107456751 A1 | 12/2017 |
| CN | 107613867 A | 1/2018 |
| CN | 108525261 A | 9/2018 |
| IN | DELNP-2012-09674 A | 7/2014 |
| JP | 2003-156994 A | 5/2003 |
| JP | 2009-226131 A | 10/2009 |
| JP | 2009-277195 A | 11/2009 |
| JP | 2018-020010 A | 2/2018 |
| KR | 10-1998-0082935 A | 12/1998 |
| KR | 10-2010-0007116 A | 1/2010 |
| KR | 10-2012-0098854 A | 9/2012 |
| KR | 10-2013-0066827 A | 6/2013 |
| KR | 10-2016-0016263 A | 2/2016 |
| KR | 20-0431902 Y1 | 11/2016 |
| KR | 2016-0130085 A | 11/2016 |
| WO | WO 2005/087323 A2 | 9/2005 |
| WO | WO 2007/048009 A2 | 4/2007 |
| WO | WO 2011/072111 A1 | 6/2011 |
| WO | WO 2013/035125 A1 | 3/2013 |
| WO | WO 2016/135183 A1 | 9/2016 |
| WO | WO 2018/075523 A1 | 4/2018 |
| WO | WO 2019/016406 A1 | 1/2019 |
| WO | WO 2021/138620 A1 | 7/2021 |
| WO | WO 2022/051272 A1 | 3/2022 |

OTHER PUBLICATIONS

Examination Report No. 1 dated Jan. 13, 2021 for Australian Application No. 2019277220, 7 pages.
Examination Report No. 2 dated Mar. 18, 2021 for Australian Application No. 2019277220, 4 pages.
Examination Report No. 1 dated Aug. 1, 2022 for Australian Application No. 2021212007, 4 pages.
Examination Report dated Apr. 29, 2022 for Canadian Application No. 3,101,984, 4 pages.
Evaluation Report dated Aug. 30, 2021 for Chinese Application No. 201921724053.2, with English translation, 20 pages.
Search Report and Written Opinion dated Oct. 25, 2021 for Singapore Application No. 11202011803X, 12 pages.
First Office Action and Search Report dated May 28, 2021 for Chinese Application No. CN201910975221.3, with English translation, 41 pages.
Second Office Action and Search Report dated Dec. 28, 2021 for Chinese Application No. 201910975221.3, with English translation, 33 pages.
Third Office Action and Search Report dated Jun. 6, 2022 for Chinese Application No. 201910975221.3, with English translation, 38 pages.
First Office Action dated Jan. 5, 2022 for Chinese Application No. 202121225607.1, with English translation, 4 pages.
First Office Action and Search Report dated Jun. 20, 2022 for Chinese Application No. 202110946212.9, with English translation, 58 pages.
Extended European Search Report dated May 25, 2021 for European Application No. 19810957.1, 7 pages.
Extended European Search Report dated Jul. 4, 2022 for European Application No. 21216666.4, 8 pages.
First Examination Report dated May 24, 2021 for Indian Application No. 202017056758, 5 pages.
Office Action dated Jun. 14, 2021 for Japanese Application No. 2020-573560, with English translation, 6 pages.

(56) References Cited

OTHER PUBLICATIONS

Notice of Preliminary Rejection dated Apr. 29, 2021 for Korean Application No. 10-2020-7037528, with English translation, 11 pages.
Notice of Final Rejection dated Feb. 9, 2022 for Korean Application No. 10-2020-7037528, with English translation, 7 pages.
Notice of Preliminary Rejection dated Apr. 14, 2022 for Korean Application No. 10-2020-7037528, with English translation, 14 pages.
International Search Report and Written Opinion dated Jul. 16, 2021 for International Application No. PCT/US2021/029786, 12 pages.
International Search Report and Written Opinion dated Feb. 24, 2022 for International Application No. PCT/US2021/048837, 32 pages.
Andreu, Y. et al., "Wize Mirror—a smart, multisensory cardio-metabolic risk monitoring system," Computer Vision and Image Understanding, 148:3-22 (2016).
Capritto, A., "Smart fitness device Mirror launches one-on-one personal training," CNET, Oct. 8, 2019, 5 pages; https://www.cnet.com/health/smart-fitness-device-mirror-launches-one-on-one-personal-training/.
Chaudhry, A., "How to watch videos with friends online," The Verge, Jul. 1, 2020, 13 pages; https://www.theverge.com/21307583/watch-videos-movies-online-friends-streaming-netflix-hulu-amazon-scener-extensions.
Choi, W. et al., "SwimTrain: Exploring Exergame Design for Group Fitness Swimming," Proceedings of the 2016 CHI Conference on Human Factors in Computing Systems, pp. 1692-1704 (May 7, 2016); retrieved at https://www.microsoft.com/en-us/research/wp-content/uploads/2016/07/p1692-choi.pdf.
"Everything You Need to Know About Throwing an obé Workout Party," Obé News, retrieved on Apr. 29, 2021 at http://obefitness.com/blog/workout-parties-faq, 8 pages.
Gartenberg, C., "Bulding your own smart mirror is surprisingly easy," Circuit Breaker, Aug. 17, 2017; Accessed at https://www.theverge.com/circuitbreaker/2017/8/17/16158104/smart-mirror-diy-raspberry-pi-commute-weather-time-gadget, 6 pages.
Magic Mirror[2]. "The open source modular smart mirror platform," Accessed at https://magicmirror.builders, Mar. 18, 2019, 4 pages.
"Mirror, mirror on the wall, is the device that livestreams exercise classes in the home any good?" Business Insider, Accessed at https:www.scmp.com/magazines/style/tech-design/article/2176110/mirror-mirror-wall-device-livestreams-exercise-classes, 17 pages.
Muoio, D., "Mirror launches its in-home fitness platform, raises another $25M from lead investor," MobiHealth News, Sep. 6, 2018, 1 page; https://www.mobihealthnews.com/content/mirror-launches-its-home-fitness-platform-raises-another-25m-lead-investor.
Perez, Sarah, "Scener now lets you co-watch HBO or Netflix in a 'virtual theater' with up to 20 people," May 2020; https://techcrunch.com/2020/05/14/scener-now-lets-you-co-watch-hbo-or-netflix-in-a-virtual-theater-with-up-to-20-people; 2020, 2 pages.
Scene, Inc., "Scener—Watch party tips: Getting started with watch parties," Jan. 2021; https://web.archive.org/web/202101232132220; https://scener.com/watch-party-tips, 2021, 40 pages.
Excerpts from "Training Mirror" video posted on YouTube, dated May 24, 2016 and accessed on May 16, 2022 at https://www.youtube.com/watch?app=desktop&v=xbgTJl7pgrg, with machine translation into English of description, 7 pages.
U.S. Appl. No. 29/704,708, filed Sep. 6, 2019.
U.S. Appl. No. 29/704,709, filed Sep. 6, 2019.
U.S. Appl. No. 17/839,609, filed Jun. 14, 2022.
U.S. Appl. No. 17/856,618, filed Jul. 1, 2022.
U.S. Appl. No. 17/856,626, filed Jul. 1, 2022.
U.S. Appl. No. 17/878,614, filed Aug. 1, 2022.
Fourth Office Action and Search Report dated Oct. 8, 2022 for Chinese Application No. 201910975221.3, with English translation, 42 pages.
Decision of Rejection dated Aug. 15, 2022 for Chinese Application No. 202121225607.1, with English translation, 5 pages.
First Examination Report dated Oct. 6, 2022 for Indian Application No. 202118053674, 4 pages.
U.S. Appl. No. 17/939,353, filed Sep. 7, 2022.
U.S. Appl. No. 17/940,202, filed Sep. 8, 2022.
U.S. Appl. No. 29/855,419, filed Oct. 3, 2022.
U.S. Appl. No. 17/959,453, filed Oct. 4, 2022.
U.S. Appl. No. 29/855,522, filed Oct. 4, 2022.
U.S. Appl. No. 17/975,710, filed Oct. 28, 2022.

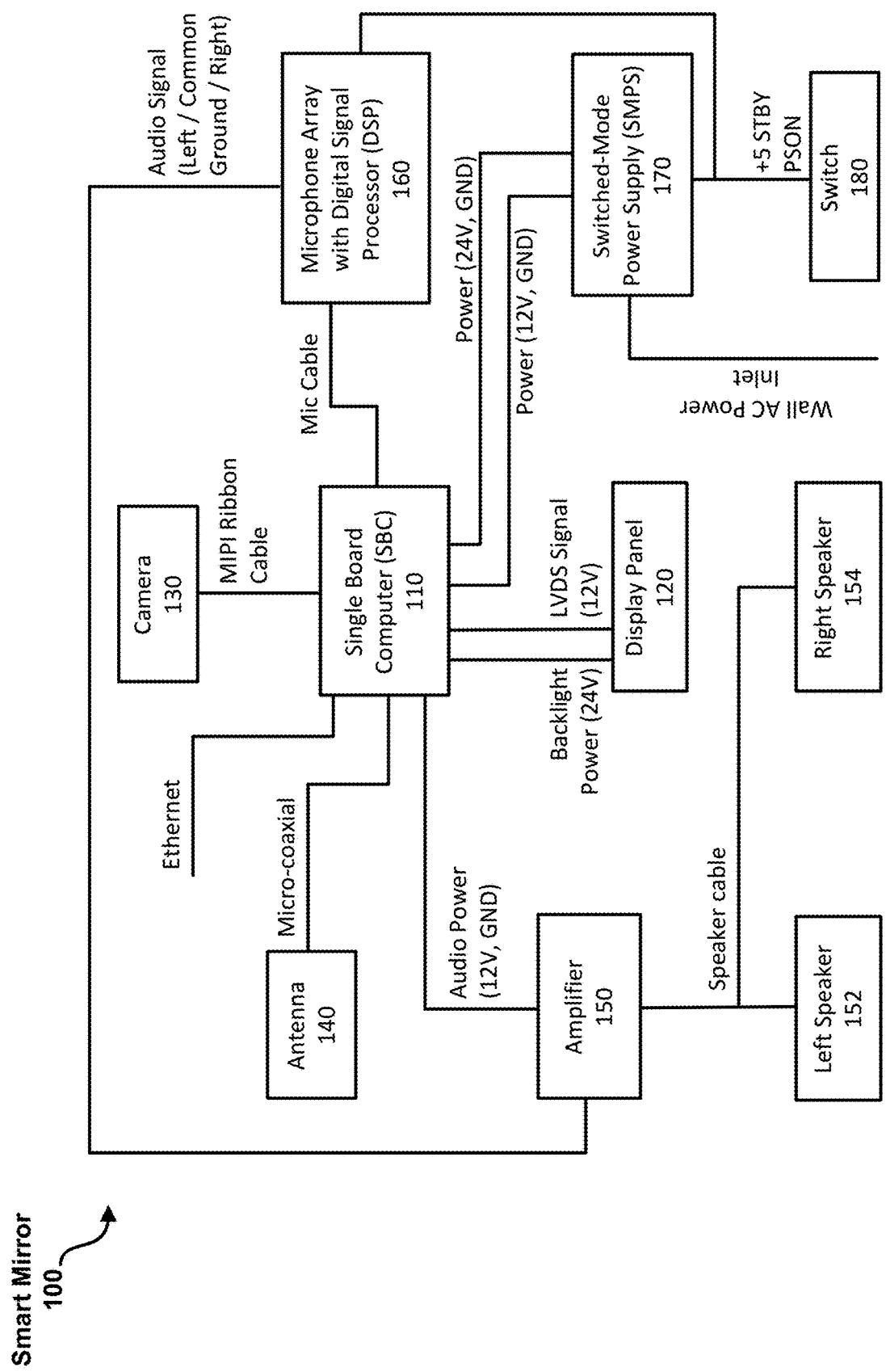

420 ⎯⧹

┌─────────────────────────────────────────┐
│ Cause display, during a first time period and via each compute
│ device from a first subset of at least two compute devices from a
│ networked plurality of compute devices, of live video depicting at
│ least one user from a first plurality of users associated with the
│ first subset of compute devices and without displaying a workout
│ video including a depiction of a workout instructor, the
│ networked plurality of compute devices including at least one
│ smart mirror and at least one mobile communication device 422
└─────────────────────────────────────────┘
                    ↓
┌─────────────────────────────────────────┐
│ Cause display, during a second time period following and mutually
│ exclusive of the first time period, and via each compute device
│ from a second subset of at least two compute devices from the
│ networked plurality of compute devices, of (1) a workout video
│ including a depiction of a workout instructor, and (2) a
│ representation of at least one user from a second plurality of
│ users associated with the second subset of compute devices 424
└─────────────────────────────────────────┘
                    ↓
┌─────────────────────────────────────────┐
│ Cause display, during a third time period following and mutually
│ exclusive of the second time period, and via each compute device
│ from a third subset of at least two compute devices from the
│ networked plurality of compute devices, of live video depicting at
│ least one user from a third plurality of users associated with the
│ third subset of compute devices 426
└─────────────────────────────────────────┘

FIG. 4C

VIDEO REBROADCASTING WITH MULTIPLEXED COMMUNICATIONS AND DISPLAY VIA SMART MIRRORS, AND SMART WEIGHT INTEGRATION

CROSS-REFERENCE TO RELATED PATENT APPLICATIONS

This application is a Continuation of U.S. patent application Ser. No. 17/315,558, filed May 10, 2022 and titled "Video Rebroadcasting with Multiplexed Communications and Display Via Smart Mirrors, and Smart Weight Integration" which claims the benefit of, and priority to, U.S. Provisional Patent Application No. 63/074,894, filed Sep. 4, 2020 and titled "Video Rebroadcasting with Multiplexed Communications and Display Via Smart Mirrors," and which claims the benefit of, and priority to, U.S. Provisional Application No. 63/144,047, filed Feb. 1, 2021 and titled "Video Rebroadcasting with Multiplexed Communications and Display Via Smart Mirrors, and Smart Weight Integration," which are related to U.S. Pat. No. 10,758,780, issued Sep. 1, 2020 and titled "Reflective Video Display Apparatus for Interactive Training and Demonstration and Methods of Using Same," the entire contents of all of which are incorporated herein by reference in their entireties.

FIELD

The present disclosure relates to systems for interactive video delivery, and more specifically, to multiplexed voice and visual communications facilitated by smart mirrors.

BACKGROUND

Exercise is an important part of maintaining an individual's health and wellbeing. For many people, exercising is an activity that typically involves going to a gymnasium where they partake in a workout guided by an instructor (e.g., a fitness instructor, a personal trainer). However, dedicating a regular period of time to exercise at a gym can be a challenging endeavor due to other commitments in one's daily life (e.g., a person's job, family obligations). Oftentimes, a gym may be located at an inconvenient location and/or an instructor's availability is limited to certain periods of time during the day, thus limiting a person's ability to attend a workout at the gym. This inconvenience may also be detrimental to the instructor whose clientele may be restricted to people who are able to attend their workout at the gym at the prescribed period of time.

SUMMARY

In some embodiments, a user of a smart mirror schedules a rebroadcast of a previously recorded fitness class, to be displayed concurrently via multiple smart mirrors associated with multiple multiplexed geographically remote users who are "invitees" to the rebroadcast. Non-invitees can be blocked from accessing the rebroadcast. During the rebroadcast, invitees and the user can view live video feeds of one another, and can communicate with one another using voice, text, and/or graphic symbols (e.g., emojis). The voice communications can occur via the microphones/speakers of the mirrors, and the text and/or graphic symbols can be displayed via the mirrors. Optionally, real-time biometric data of the user can be displayed via the user's smart mirror and/or via smart mirrors of other invitees.

BRIEF DESCRIPTION OF THE DRAWINGS

FIG. 1 is a block diagram of a smart mirror, in accordance with some embodiments.

FIG. 4C is a flow diagram of an example method of hosting a locker room session on networked compute devices, in accordance with some embodiments.

DETAILED DESCRIPTION

Figure 2C:
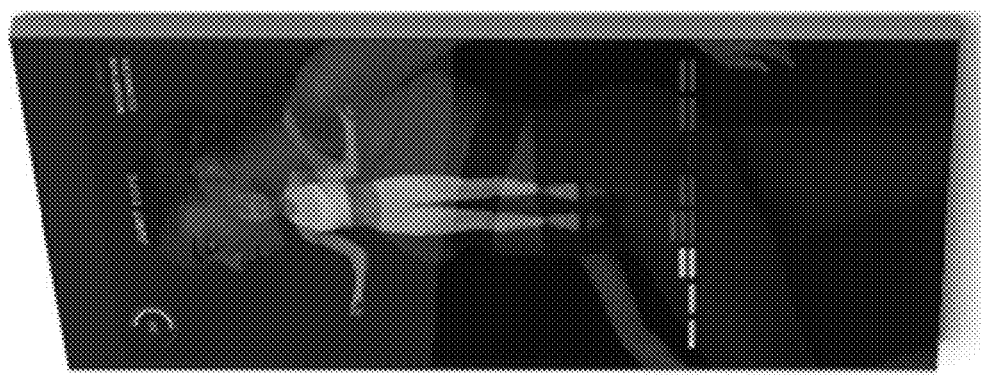
FIG. 2C shows a third, wall-mountable example implementation of a smart mirror, in accordance with some embodiments.

The demand for home fitness products has been increasing for years, and in the midst of widespread public health concerns arising from Covid-19, forcing many to self-quarantine, such demand, in particular for "interactive" home fitness products, has been further enhanced. Known approaches to interactive fitness, however, typically involve a user interacting with a software application running on a smartphone, making it difficult to coordinate movements with the ability to clearly view the instruction rendered via the smartphone screen. In addition, many known approaches to streaming fitness content (e.g., via smart televisions) are not interactive (i.e., they involve one-way delivery of streamable content to viewers), and can exhibit low and/or inconsistent video resolution/quality, bandwidth limitations, latency issues, reliability issues (e.g., video dropout) buffering delays, video stream stuttering, device incompatibilities, etc. Embodiments set forth herein overcome the foregoing limitations of known approaches to delivering fitness content in a variety of ways, as discussed in the sections that follow.

Smart Mirrors

A "smart mirror," as used herein, refers to a two-way mirror (e.g., comprising glass) and an electronic display that is at least partially aligned with (and disposed behind, from the point of view of a user) the two-way mirror, such that the user can simultaneously view his/her own reflection and the imagery/video presented via the electronic display during operation of the smart mirror. FIG. 1 is a block diagram of a smart mirror 100, in accordance with some embodiments. The smart mirror 100 includes a single board computer (SBC) 110 that controls, at least in part, the operation of various subcomponents of the smart mirror 100 and to manage the flow of content to/from the smart mirror 100 (e.g., video content, audio from one or more instructors and/or users, biometric sensor data, etc.). The smart mirror 100 includes a display panel 120 configured to display video content and a graphical user interface (GUI) with which users may interact to control the smart mirror 100, for example to view biometric feedback data and/or other visual content, to select content for display, etc. The smart mirror 100 also includes a camera 130 operably coupled to the SBC 110 and configured (e.g., under control of the SBC 110) to record or live stream video and/or images of a user (e.g., while the user is exercising during a workout session). An antenna 140 is operably coupled to the SBC 110 and configured to facilitate communications between the smart mirror 100 and another device (e.g., a remote compute device, one or more other smart mirrors, a remote control device, one or more biometric sensors, a wireless router, one or more mobile compute devices, etc.) by transmitting and receiving signals representing messages. The antenna 140 can include multiple transmitters and receivers each configured to transmit/receive at a specific frequency and/or using a specific wireless standard (e.g., Bluetooth®, 802.11a, 802.11b, 802.11g, 802.11n, 802.11 ac, 2G, 3G, 4G, 4G LTE, 5G). The antenna 140 may include multiple antennas that each function as a receiver and/or a transmitter to communicate with various external devices, such as a user's smart device (e.g., a computer, a smart phone, a tablet), a biometric sensor (e.g., a heart rate monitor, a vibration sensor, or any other sensor described herein), and/or a remote server or cloud server to stream or play video content. An amplifier 150 is operably coupled to the SBC 110, a left speaker 152, a right speaker 154, and a microphone array with a digital signal processor 160, The amplifier 150 is configured to receive audio signals from the SBC 110 and route them for subsequent output through the left speaker 152 and/or the right speaker 154. The microphone array 160 can be configured to detect audio/voice, including voice commands and/or other voice inputs made by one or more users within sufficient proximity of the smart mirror 100. For example, the microphone array 160 can detect voice commands to start/stop a workout, voice communications to the instructor, voice commands to turn the display panel on/off, voice commands to change a layout of the GUI, voice commands to trigger an invitation to another smart mirror user to participate in a workout session, etc. The microphone array 160 is operably coupled to, and controllable by, the SBC 110. A switched-mode power supply (SMPS) 170 is coupled to the SBC 110 and coupled to relay (and, optionally, regulate delivery of) electrical power from an external electrical power supply system (e.g., a wall outlet) to the various components of the smart mirror 100. A switch 180 may be coupled to the SMPS 170 and/or the microphone array 160 to switch the smart mirror 100 and the microphone array 160 on and off Although shown and described in FIG. 1 as including a single board computer 110, in other embodiments the smart mirror 100 can include one or multiple processors and one or multiple memories operably coupled to the one or multiple processors.

In some embodiments, the smart mirror 100 also includes one or more additional components not shown in FIG. 1. For example, the smart mirror 100 may include onboard memory storage (nonvolatile memory and/or volatile memory) including, but not limited to, a hard disk drive (HDD), a solid state drive (SDD), flash memory, random access memory (RAM), or a secure digital (SD) card. This onboard memory storage may be used to store firmware and/or software for the operation of the smart mirror 100. As described above, the onboard memory storage may also be used to store (temporarily and/or permanently) other data including, but not limited to, video content, audio, video of the user, biometric feedback data, and user settings. The smart mirror 100 may also include a frame to mount and support the various components of the smart mirror 100.

Figure 2B:
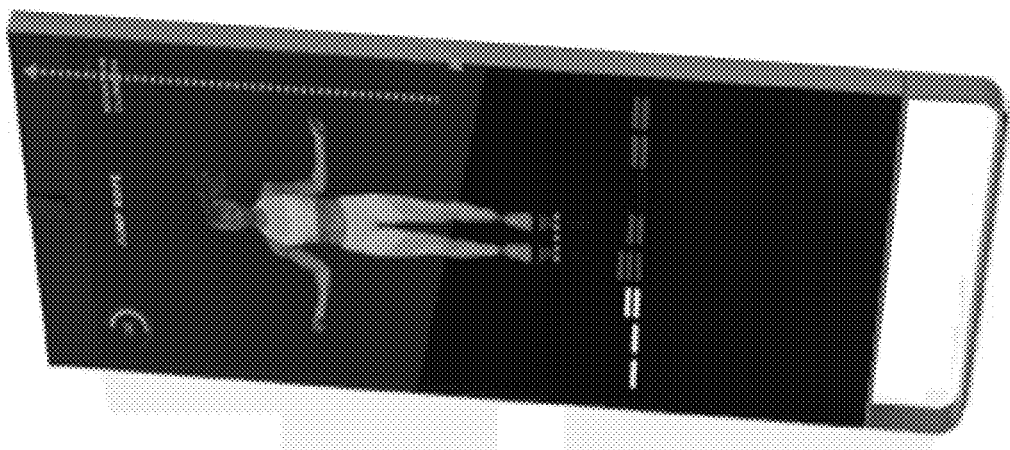
FIG. 2B shows a second example implementation of a smart mirror, with an integrated stand, in accordance with some embodiments.
Figure 2A:
FIG. 2A shows a first example implementation of a smart mirror, in accordance with some embodiments.

Smart mirrors of the present disclosure may be positioned or mounted within an environment (e.g., a user's home, a fitness studio) in a variety of ways. FIG. 2A shows a first example implementation of a smart mirror, in accordance with some embodiments. FIG. 2B shows a second example implementation of a freestanding smart mirror, with an integrated stand, in accordance with some embodiments. FIG. 2C shows a third, wall-mountable example implementation of a smart mirror, in accordance with some embodiments. FIGS. 2A and 2B show the smart mirror mounted to a stand positioned at the bottom of the smart mirror. As can be seen in FIG. 2A, the smart mirror reflects (via a semi-reflective or partially reflecting surface thereof) an image of a user (here, taking a picture of the smart mirror with a smart phone) and the surrounding environment. The smart mirror of FIG. 2A also displays video content through the semi-reflective or partially reflecting surface, such that the video content and the reflections of the user and the surrounding environment are concurrently viewable via the smart mirror. When the smart mirror is powered off, the smart mirror has a fully reflective appearance under ambient lighting. In some implementations, the smart mirror includes a partially reflecting section and a fully reflecting section (e.g., surrounding the partially reflecting section).

Video Rebroadcasting Sessions with Multiplexed Smart Mirror Communications ("Sweat Dates")

In some embodiments, a previously-recorded ("archived") video including fitness content is made available (e.g., via a cloud-based server) to, or is accessible by, a networked plurality of smart mirrors. The previously-recorded video can be a previously-aired or previously broadcast class from a library of classes stored in the cloud-based server or other storage repository. The previously-recorded video may have been captured "live" via a smart mirror camera, or may have been recorded offline (e.g., in a fitness recording studio). One or more users ("scheduler(s)") of the smart mirrors can schedule a broadcasting or rebroadcasting "session" (hereinafter "video rebroadcasting session") of the previously-recorded video during a specified time interval, and invite other smart mirror users from a selected group of other smart mirror users (invitees) to join the session and watch the broadcast/rebroadcast simultaneously during the specified time interval. By interacting with a software application ("app") running on a mobile device (e.g., a smartphone) and/or a smart mirror, the scheduler(s) can specify one or more of the following parameters for the video rebroadcasting session ("session data"): a start date, a start time, an end date, an end time, identifiers of user(s) that are invited to participate in the video rebroadcasting session ("invitees"), overlays to be presented to the invitees during the video rebroadcasting session, etc. The invitees can include all subscribers or users of smart mirrors within a networked community of smart mirrors, or a subset thereof. In some implementations, non-invitee smart mirror users are blocked from joining the video rebroadcasting session (e.g., by setting a "rule" that is stored in the cloud-based server or another repository accessible by and used by the app).

During the video rebroadcasting session, the scheduler and the invitees position themselves near their respective smart mirrors and view the previously-recorded video, which is displayed concurrently on the smart mirrors of all invitees, while simultaneously viewing "live" (i.e., real-time or substantially real-time) video of themselves and, optionally, the scheduler and/or one or more other invitees. Also during the video rebroadcasting session, the scheduler and the invitee(s) can interact with one another via their respective smart mirrors, e.g., visually (e.g., by gesturing within the field of view of the cameras of their respective smart mirrors, the gestures being viewable via the smart mirror(s) or one or more invitees), images (e.g., causing display of photos/images on smart mirrors of one or more invitees), voice (e.g., via the microphone(s) and speaker(s) of their respective smart mirrors), and/or by inputting feedback via the app (e.g., via a graphical user interface (GUI) of the app running on their smart mirror and/or via a GUI of the app running on their smartphone). As such, the smart mirrors, the scheduler, and the invitees (some or all of which are geographically remote from one another), as well as their communications with one another, are multiplexed within a networked system (e.g., as shown and discussed with reference to FIG. 3A, below). The feedback can include text and/or graphic symbols (e.g., emojis) that is subsequently displayed via the app of one or more invitees (e.g., via a GUI of the app running on their smart mirror and/or via a GUI of the app running on their smartphone). The disclosed system therefore facilitates multiplexed communications between and among the scheduler and the invitees, who may be geographically remote from one another. Optionally, real-time biometric data of the scheduler and/or the invitees can be displayed via a smart mirror of the scheduler and/or the invitees.

Figure 3A:
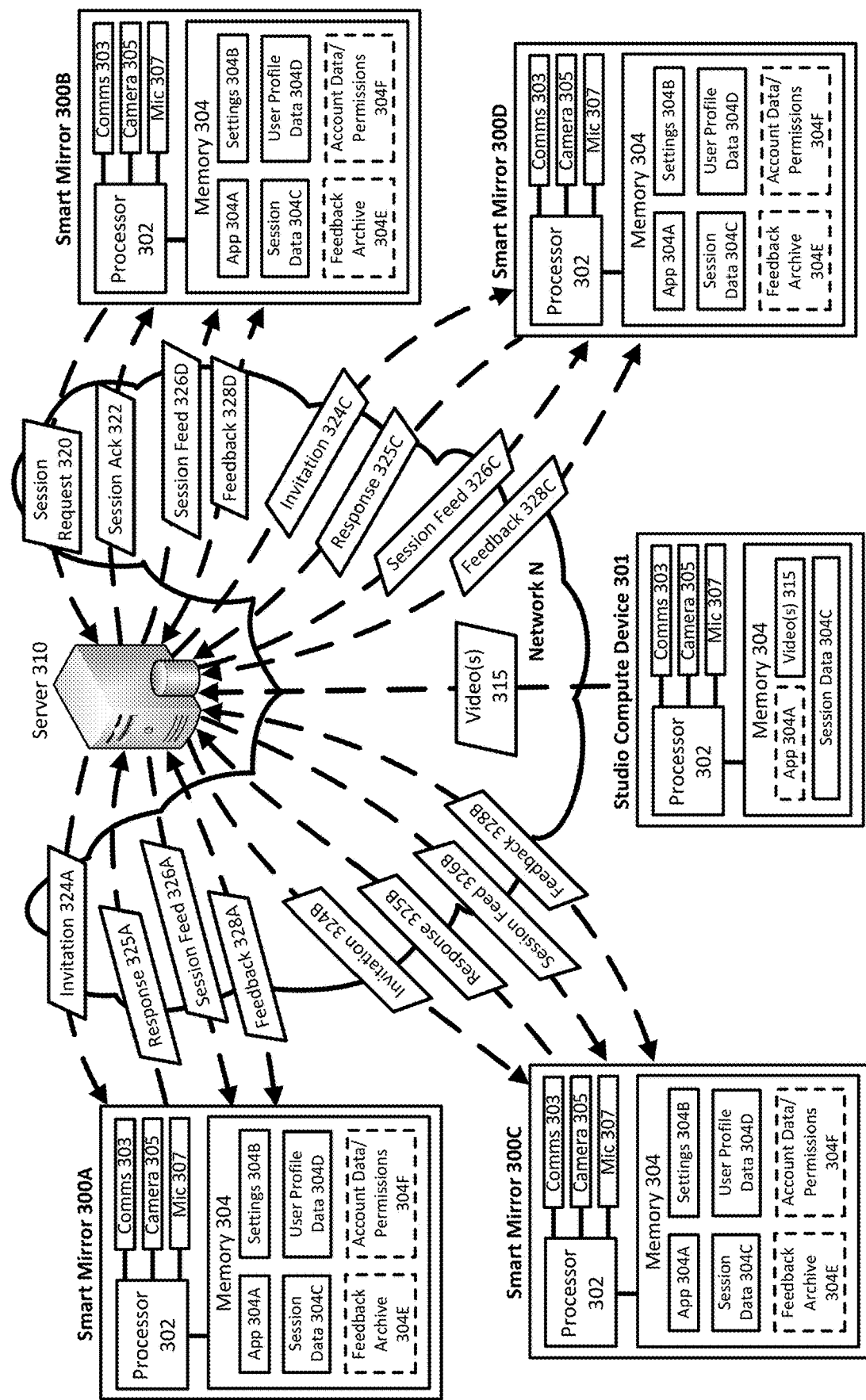
FIG. 3A is an example flow diagram showing multiplexed communications during a video rebroadcasting session, in accordance with some embodiments.

FIG. 3A is an example flow diagram showing multiplexed communications associated with scheduling and hosting a video rebroadcasting session, in accordance with some embodiments. As shown in FIG. 3A, each of multiple smart mirrors (300A, 300B, 300C and 300D) and an optional studio compute device 301 can communicate with a centralized server 310 (e.g., a cloud-based server including a processor and a memory storing processor-executable instructions to perform method steps described herein) via a network "N." The network N can be a fully wireless telecommunications network, a fully wired telecommunications network, or a combination of both. The studio compute device 301 can be a desktop computer, laptop computer, tablet and/or smartphone, and can be located in a recording studio or other location suitable for recording video and audio for live and/or subsequent broadcast. The smart mirrors 300A, 300B, 300C and 300D can be similar to, or include some or all of the components of, the smart mirror 100 of FIG. 1. As shown in FIG. 3A, each of the smart mirrors 300A, 300B, 300C and 300D includes a processor 302, communications component(s) 303 (e.g., one or more antennas, transceivers, etc.), a memory 304, a video camera 305, and at least one microphone (e.g., a microphone array) 307. Each memory 304 stores an instance of a shared software application ("app" 304A), settings 304B (e.g., user-customizable settings for that smart mirror), session data 304C (e.g., including data associated with past video rebroadcasting sessions and/or future video rebroadcasting sessions), user profile data 304D for the user(s) associated with that smart mirror, and optionally a feedback archive 304E and/or account data and permissions 304F. The studio compute device 301 includes a processor 302, communications component(s) 303 (e.g., one or more antennas, transceivers, etc.), a memory 304, a video camera 305, and at least one microphone (e.g., a microphone array) 307. The memory 304 of the studio compute device 301 stores session data 304C, video(s) 315, and, optionally, an instance of the shared software application ("app" 304A). The session data 304C can include, for example, one or more of: class name(s), instructor name(s), original recording date, original recording time, number of times rebroadcast (i.e., number of previous video rebroadcasting sessions and/or future video rebroadcasting sessions), scheduled future rebroadcast date(s), scheduled future rebroadcast time(s), scheduled future rebroadcast duration(s), scheduled future rebroadcast participants/invitees, scheduled future rebroadcast scheduler(s), etc. In some implementations, the studio compute device 301 is a smart mirror.

According to some embodiments, prior to scheduling a video rebroadcasting session, one or more videos 315 (optionally recorded via the camera 305 of the studio compute device by an instructor user of the studio compute device 301) are sent to the server 310, via the network N, from the studio compute device 301. The one or more videos 315 can be stored in a memory of the server 310 for later retrieval by one or more users of the smart mirrors 300A, 300B, 300C and 300D. The users of the smart mirrors 300A, 300B, 300C and 300D can also browse the one or more videos 315 stored in the memory of the server 310 via the shared app 304 on their respective smart mirrors and/or via instances of the shared app 304 running on their respective smart phones or other mobile compute device(s). Although the one or more videos 315 are shown and described, with reference to FIG. 3A, as being sent to the server 310 from (and optionally recorded via) the studio compute device 301, alternatively or in addition, the one or more videos 315 can be sent to the server 310 from (and optionally recorded via) one or more of the smart mirrors 300A-300D. In such embodiments, the one or more videos can features the user(s) (e.g., performing workouts) rather than an instructor.

As shown in FIG. 3A, the scheduling of a video rebroadcasting session begins with a session request 320 sent from one of the networked smart mirrors (in this case, smart mirror 300B), via the network N, to the server 310. The session request 320 can be generated and sent in response to an input or interaction of a user of the smart mirror 300B via the shared app 304 running on the smart mirror 300B and/or via an instance of the shared app 304 running on the smart phone or other mobile compute device of the user. A user (or a smart mirror associated with that user) that causes generation of a session request 320 can be referred to as a "scheduler." The session request 320 can include one or more video identifiers associated with the videos 315, one or more user identifiers associated with the scheduler(s), and/or representations of one or more: class names, instructor names, original recording dates, original recording times, number of times rebroadcast (i.e., number of previous video rebroadcasting sessions and/or future video rebroadcasting sessions), skill levels, muscle groups, requested future rebroadcast date(s), requested future rebroadcast time(s), requested future rebroadcast duration(s), requested future rebroadcast participants/invitees, etc. The server 310 can maintain a local calendar or other schedule of past, current and/or future video broadcasts and rebroadcasts. The server 310, upon receiving (and in response to) the session request 320, can compare data from the session request with data stored in the memory of the server 310 to determine whether the requested video rebroadcasting session can be scheduled. If so, the server 310 may store, in the calendar or other schedule, a new data record associated with the video rebroadcasting session. Also in response to receiving the session request, the server 310 generates and sends, to the smart mirror 300B and via the network N, a session acknowledgment message 322. The session acknowledgment message 322 can include an indication as to whether the video rebroadcasting session has been approved/scheduled, a confirmation number for the request and/or acknowledgment, and if scheduled, scheduling information. Optionally, if a requested video rebroadcasting session has not been scheduled, or has been disapproved, the session acknowledgment message 322 can include suggestions for alternative scheduling, e.g., including any of the data types included in the session request.

If the smart mirror 300B receives a session acknowledgment message 322 indicating that the video rebroadcasting session has not been scheduled, one or more session requests 320 may be sent from the smart mirror 300B to the server 310, in response to one or more of: a user selection of new session details made via the shared app, a user selection of a suggested alternative scheduling made via the shared app, or an automatic instruction generated by the smart mirror 300B based on a rule within the settings 304B of the smart mirror 300B.

If the session acknowledgment message 322 indicates that the video rebroadcasting session has been scheduled, the server 310 (and/or the smart mirror 300B or a mobile device operably coupled thereto) can send, either subsequently to or concurrently with sending the session acknowledgment message 322, invitation messages to smart mirrors associated with users that are invited to the scheduled video rebroadcasting session (e.g., as specified by the session request 320). In this case, invitations 324A, 324B and 324C are sent to smart mirrors 300A, 300C and 300D, respectively. Once received at the respective smart mirrors, the invitations can trigger the display, via the shared app 304A of the smart mirrors and/or via the shared app 304A of mobile devices (optionally operably coupled to the smart mirrors), a user-selectable option to accept an invitation to join the scheduled video rebroadcasting session. Response messages 325A, 325B and 325C are generated based on the users' selections, and sent back to the server 310 which, in turn, can update the new data record associated with the video rebroadcasting session, to indicate a participation status (e.g., "accepted" or "declined") for each of the users and/or smart mirrors. At the scheduled session start time, the server 310 can initiate and transmit a session feed (e.g., session feeds 326A, 326B, 326C and/or 326D), or a streamed version of the video(s) associated with the one or more video identifiers of the session request, to each smart mirror associated with an "accepted" participation status. Note that in some implementations, the scheduler(s) is automatically assigned an "accepted" participation status and sent the session feed during the video rebroadcasting session, while in other implementations the scheduler(s) is not automatically assigned an "accepted" participation status and/or the session request 320 includes a representation of a participation status for the scheduler(s). During the video rebroadcasting session, the session feeds 326A, 326B, 326C and/or 326D cause display of the video(s) associated with the one or more video identifiers of the session request via the associated smart mirrors 300A, 300C, 300D and/or 300B. Also during the video rebroadcasting session, users of the smart mirrors 300A, 300C, 300D and/or 300B can send feedback (328A, 328B, 328C and/or 328D, respectively) to the smart mirror(s) of one or more other invitees, optionally subject to settings 304B and/or permissions 304F of the smart mirror(s) of one or more other invitees. The feedback can include text, images, graphics (e.g., emojis), voice and/or video that is displayed or otherwise delivered via the smart mirror(s) (and/or associated mobile device(s)) of the recipient(s). Optionally, feedback that is sent or exchanged during the video rebroadcasting session is stored in the feedback archive(s) 304E by the smart mirror(s) of one or more smart mirrors (300A, 300C and/or 300D) of the invitees. The feedback can be stored in the feedback archive(s) 304E in the form of records that include feedback date/time data, sender data, recipient data, session data and/or other data associated with the feedback, such that the feedback can subsequently be retrieved, viewed and/or displayed. The sender data can include sender identifier(s), sender biometric data, sender location data, sender fitness level data, etc. Similarly, the recipient data can include recipient identifier(s), recipient biometric data, recipient location data, recipient fitness level data, etc.

Figure 3C:
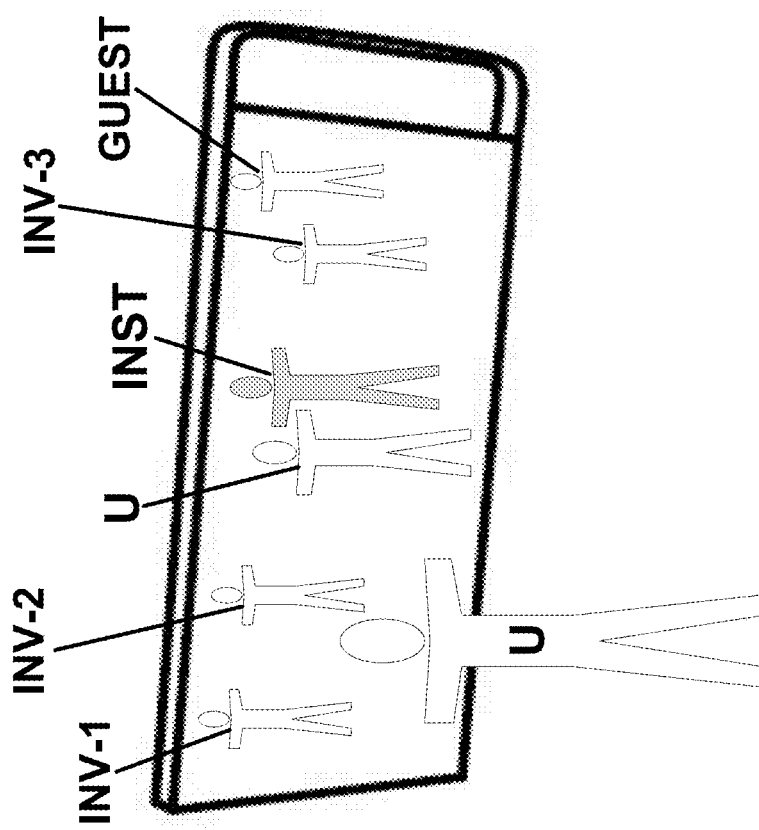
FIGS. 3B-3C show example display configurations for a video rebroadcasting session, in accordance with some embodiments.
Figure 3B:
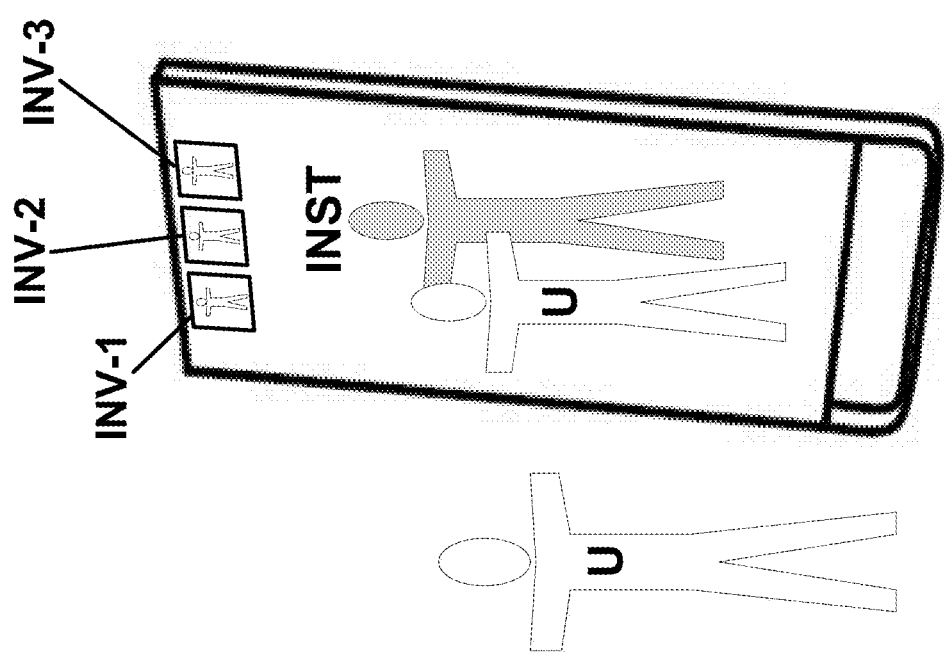

FIGS. 3B-3C show example display configuration for a video rebroadcasting session, in accordance with some embodiments. In a first embodiment, shown in FIG. 3B, while a session feed 326A-326D is being transmitted/fed to the smart mirrors 300A-300D during the video rebroadcasting session described with reference to FIG. 3A, a user "U" of a given smart mirror (e.g., smart mirror 300B) can view, concurrently and in/on a common surface of the smart mirror: (1) a reflection of himself/herself ("U"), (2) the video feed showing the pre-recorded video (e.g., including an instructor "INST"), and optionally (3) live video of one or more other invitees (here, "INV-1" through "INV-3"), captured by the smart mirrors (300A, 300C and/or 300D) of those invitees. As shown in FIG. 3B, the invitees can be presented in discrete panes arranged within the display of the common surface of the smart mirror. The panes can be arranged in a horizontal row along a smaller of a height or width of the smart mirror (as shown in FIG. 3B), or alternatively in a horizontal row along a larger of the height or width of the smart mirror, in a vertical row along a smaller of the height or width of the smart mirror, in a vertical row along a larger of the height or width of the smart mirror, or in any other (optionally user-specified and/or reconfigurable) configuration. Optionally, the smart mirror has touch-screen functionality, such that user "U" can select (by touching the image of) one of the other invitees "INV-1" through "INV-3" to cause the associated live video pane to be resized (e.g., enlarged, reduced) within the smart mirror display, to close (i.e., stop display of) the associated live video pane, etc. Alternatively or in addition, the user U can view some or all components of the video rebroadcasting session via an instance of the shared app on his/her mobile compute device and interact with the video panes using the associated GUI of the mobile compute device, such that the video panes are resized or closed on the smart mirror. In other words, in response to a user manipulation of a video pane in a GUI of his//her mobile compute device, the shared app can cause the smart mirror to adjust the way that the video pane is rendered on the smart mirror.

In a second embodiment, shown in FIG. 3C, while a session feed 326A-326D is being transmitted/fed to the smart mirrors 300A-300D during the video rebroadcasting session described with reference to FIG. 3A, a user "U" of a given smart mirror (e.g., smart mirror 300B) can view, concurrently and in/on a common surface of the smart mirror that may be oriented in a "landscape" format (i.e., the width is larger than the height): (1) a reflection of himself/herself ("U"), (2) the video feed showing the pre-recorded video (e.g., including an instructor "INST"), and optionally (3) live video of one or more other invitees (here, "INV-1" through "INV-3"), captured by the smart mirrors (300A, 300C and/or 300D) of those invitees. As shown in FIG. 3C, the live video images of the invitees can be presented within the common surface of the smart mirror (not in panes) and arranged (e.g., dimensioned) such that the invitees are similar in size to, or at least 50% the size of, the size of the reflected image of user U, thereby simulating a live "class" environment. As also shown in FIG. 3C, one or more "guest" users may be sufficiently permissioned (or request permission in realtime) to join an ongoing video rebroadcasting session, and may be labelled as such within the smart mirror display. Similar to the embodiment of FIG. 3B, the smart mirror optionally has touch-screen functionality, such that user "U" can select (by touching the image of) one of the other invitees "INV-1" through "INV-3" to cause the associated live video to be resized (e.g., enlarged, reduced) within the smart mirror display, to close (i.e., stop display of) the associated live video, etc. Alternatively or in addition, the user U can view some or all components of the video rebroadcasting session via an instance of the shared app on his/her mobile compute device and interact with the live video of the invitees using the associated GUI of the mobile compute device, such that the live video images are resized or closed on the smart mirror. In other words, in response to a user manipulation of a live video image in a GUI of his//her mobile compute device, the shared app can cause the smart mirror to adjust the way that the live video is rendered on the smart mirror.

Camera Activation in Mirror Device

In some embodiments, a live video/camera feed of a first smart mirror (e.g., smart mirror 100 of FIG. 1) from a networked plurality of smart mirrors (e.g., smart mirrors 300A-300D of FIG. 3A) is transmitted (as a "live stream") to one or multiple other smart mirrors from the networked plurality of smart mirrors, for example via a wired or wireless network (e.g., network N of FIG. 3A) and via a server (e.g., server 310 of FIG. 3A). The live streaming can be selectively turned on and off by the user of the first smart mirror and/or by the users of the one or multiple other smart mirrors from the networked plurality of smart mirrors, for example, according to permissions. The action of turning on or off the live stream can be in response to one or more of: an interaction by a user with an instance of a shared app on the smart mirror, an interaction by a user with an instance of a shared app on a mobile compute device, a voice/nose command made by a user via an instance of a shared app on the smart mirror, a voice/noise command made by a user via an instance of a shared app on a mobile compute device, a gesture command made by a user via an instance of a shared app on the smart mirror, a gesture command made by a user via an instance of a shared app on a mobile compute device, etc. The live stream can be captured by one or more smart mirrors from the streaming feed to produce captured video, and the captured video can be modified post-capture to remove and/or to add graphical elements, thereby producing modified captured video. The graphical elements can be images or animations that modify the user or the environment around the user (e.g. obscuring a user's background, modifying a user's appearance, overlaying one or more filters, and/or adding one or more dynamic effects (e.g., an augmented reality (AR) feature such as a pet or a crackling fire)). The captured video and/or the modified captured video can be sent from the smart mirror(s) to a remote server (e.g., a cloud server, such as server 310 in FIG. 3A), for example for subsequent retrieval, rebroadcast, etc.

Encouragement Messaging:

In some embodiments, during a workout session, a video rebroadcasting session, and/or a "locker room" session (discussed further below), smart mirror users can cause the display of encouragement messages (e.g., including text, images, video, graphics (e.g., emojis), gestures, voice, animation, etc.) to be displayed in the smart mirrors and/or mobile compute devices (e.g., via a GUI of a shared app running thereon) of other smart mirror users within a networked plurality of smart mirrors. The encouragement messages can be generated and sent from a sender compute device (e.g., smart mirror, app, or smartphone) in response to an input or interaction of a user of a given smart mirror via a shared app running on that smart mirror and/or via an instance of the shared app 304 running on a smart phone or other mobile compute device of the user. Encouragement messages can be sent between individual users (i.e., one-to-one), for example between workout session participants and/or between an instructor and a workout session participant, or from a single user to multiple users, up to the entire community of users (i.e., one-to-many). Encouragement messages can be stored in memory, e.g., in the form of records that include feedback date/time data, sender data, recipient data, session data, workout data, maliciousness score(s), offensiveness score(s), sentiment score(s), and/or other data associated with the encouragement messages, such that the encouragement messages can subsequently be retrieved, viewed and/or displayed. The encouragement messages can be stored automatically, according to a user-defined rule, and/or in response to a user request. The encouragement messages can be stored in a memory of one or more smart mirrors, one or more remote servers (e.g., cloud servers), and/or one or more mobile compute devices.

Encouragement messages, once received at smart mirrors and/or mobile compute devices, may first be inspected, and a determination may be made as to whether the sender, a smart mirror or mobile compute device of the sender (i.e., a sender device), and/or the message contents are sufficiently permissioned or have previously been "whitelisted" such that they may be delivered or presented to the intended recipient. For example, the smart mirror and/or mobile compute device, via a processor thereof and/or via a shared app, can perform one or more of the following inspections/checks: analyze the message contents to determine a maliciousness score, analyze the message contents to determine an offensiveness score, analyze the message contents to determine a sentiment score, evaluate the message contents based on a set of rules or permissions, compare a sender identifier to stored sender data to determine whether the associated sender has been whitelisted, blacklisted, or has one or more associated permissions, compare a sender device identifier to stored device data to determine whether the associated sender device has been whitelisted, blacklisted, or has one or more associated permissions, etc. After the inspections/checks have been performed, the smart mirror and/or mobile compute device, via a processor thereof and/or via a shared app, can perform one or more of the following remediation actions: block delivery of the encouragement message to the recipient (e.g., prevent display of the encouragement message), send a reply message to the sender to indicate that the encouragement message has not been delivered, etc. The remediation actions can be performed in response to one or more triggers, which can include, but are not limited to: a maliciousness score exceeding a predefined, user-customizable threshold, detecting that the sender is has been blacklisted, detecting that the sender device has been blacklisted, detecting a rule that prevents delivery of messages from the sender, detecting a rule that prevents delivery of messages from the sender device, detecting a rule that prevents delivery of messages containing one or more predefined, user-customizable keywords, detecting a rule that prevents delivery of messages containing profanity, etc.

As used herein, a maliciousness score can be a numerical score that is generated using a machine learning algorithm configured to detect malware, spyware, spam and other unwanted messages. As used herein, an offensiveness score can refer to a numerical score that is generated based on one or more of: a linguistic model, one or more previous ratings assigned by the intended recipient user, a user-customizable sensitivity score associated with the intended recipient user, etc. As used herein, a sentiment score can refer to a numerical score (including positive values and negative values) generated by a machine learning model, the numerical score representing an overall sentiment or tone (e.g., angry, menacing, passive-aggressive, sarcastic, encouraging, happy, etc.) of an input message.

In some embodiments, encouragement messages are sent after a sender-specified time delay or at a sender-specified scheduled date/time or period (e.g., during a class scheduled for the next day). Alternatively or in addition, the display of encouragement messages received at a smart mirror (or app thereof) of a recipient may be delayed by, or blocked for, a recipient-defined period of time or until a user-defined event occurs or has transpired (e.g., after class to avoid distraction).

In some embodiments, encouragement messages are sent automatically to a first smart mirror (e.g., from a server and/or from one or more other smart mirrors), in response to detecting that one or more predefined conditions have been meet and/or that one or more rules have been satisfied. Examples of rules can include, but are not limited to: a rule to send encouragement messages to recipients that are friends and that that have set a new record within a predetermined preceding time period; a rule to send an encouragement message to a recipient in response to detecting that a performance metric (e.g., heart rate, intensity, breathing rate, cadence, power, etc.) of the recipient has reduced by at least a predetermined percentage within a predetermined period of time; a rule to send an encouragement message to a recipient in response to detecting that a workout session in which the recipient is participating is within a predetermined of time of an end time of the workout session (e.g., nearing the end of the workout session or a high-intensity portion thereof), a rule to randomly send encouragement messages (e.g., the timing, recipient and/or contents of the encouragement messages can be randomly selected), etc. Examples of conditions can include, but are not limited to: the existence of a friend relationship between the sender and the receiver; the existence of one or multiple social media connections between the sender and the receiver; fewer than a predetermined number of encouragement messages sent within a preceding predetermined period of time, etc.

In some embodiments, encouragement messages can be configured to "persist" within a GUI of the recipient (e.g., in the smart mirror of the recipient and/or in a smartphone or other mobile device of the recipient). As used herein, "persist" can refer to the continuous display for a predetermined extended period of time (e.g., greater than one minute, greater than five minutes, greater than ten minutes, for the duration of a workout session, until the smart mirror is turned off, or indefinitely) and/or until closed or minimized by the recipient. For example, in some such embodiments, an encouragement message is configured to display as a banner having at least one dimension that is the same as a width or a height of the smart mirror and/or having at least one dimension that is the same as a width or a height of the display panel of the smart mirror. In some such implementations, an encouragement message (e.g., in the form of a banner) persists within a portion of a display panel of a smart mirror when the remainder of the display panel is no longer displaying video (i.e., the remainder of the display panel has a mirror appearance).

In some embodiments, a smart mirror (or an app thereof) is configured to convert one or more encouragement messages, received from a sender from a first, as-received format, to a user-defined (i.e., recipient-defined) format that is different from the as-received format, either based on one or more rules stored in memory or based on an input received at the smart mirror and/or via the app from the user/recipient. Examples of as-received formats and user-defined formats include, but are not limited to: text, image, bitmap (e.g., Graphics Interchange Format ("GIF")), animated GIF, video, audio, haptic/vibration feedback, Adobe Flash, watermark, etc. In some such embodiments, the rules stored in memory and/or the input from the user/recipient include instructions to present the encouragement messages using one of a display panel or a speaker of the smart mirror, or to cause communication of the encouragement messages to a recipient using an antenna of the smart mirror (e.g., by transmitting a signal to one or more compute devices, apps, or smart accessories in network communication with the smart mirror).

As a first example, a received encouragement message including a visual hand clap emoji can be converted to an audio hand clap that is played via the left speaker and/or the right speaker of the smart mirror. As a second example, a received encouragement message including a text message can be converted to a graphic image that is displayed via the display panel of the smart mirror. As a third example, a received encouragement message including an audio file (e.g., including a representation of speech or of sounds such as clapping) can be converted to text that is displayed via the display panel of the smart mirror. As a fourth example, a received encouragement message including image data can be converted to a GIF that is displayed via the display panel of the smart mirror. As a fifth example, a received encouragement message including graphic image data (e.g., an emoji) can be converted to a signal that is sent, via an antenna of the smart mirror, to an app running on a smart phone of the recipient, to cause display of a reduced-size image based on the graphic image data. As a sixth example, a received encouragement message including a text message can be converted to a signal that is sent, via an antenna of the smart mirror, to a wearable electronic accessory of the recipient (e.g., a bracelet) to cause a vibration (e.g., in a predefined pattern, with a predefined intensity, etc.) of the wearable electronic accessory. As a seventh example, a received encouragement message including a text message can be converted to a log file that is stored within a memory of the smart mirror (or in a remote server communicatively coupled to the smart mirror), for later retrieval/viewing. As an eighth example, a received encouragement message including a text image and/or image file can be converted into a social media post that is sent, via an app, for posting on one or multiple social media platforms (e.g., according to one or more predefined rules, which may specify privacy settings, post timing, automatic caption generation, rules for tagging other social media users, etc.).

In some embodiments, the smart mirror, app and/or mobile compute device associated with the smart mirror is configured to automatically generate and send a reply message (e.g., including another encouragement message, acknowledging receipt of the encouragement message, expressing gratitude for the encouragement message, etc.) to the sender compute device associated with the encouragement message.

In some embodiments, the smart mirror, app and/or mobile compute device stores rules or filters configured to block delivery, display, or presentation of an encouragement message in response to determining that a sentiment score, calculated for the encouragement message, is associated with an overall sentiment or tone of for example angry, menacing, passive-aggressive, or sarcastic.

In some embodiments, a smart mirror, app and/or mobile compute device can store rules or filters configured to block sending, delivery, display, or presentation of an encouragement message in response to detecting one or more predefined recipient conditions, which may include (but are not limited to): poor performance in a workout (e.g., a performance metric, optionally correlated to one or more biometric data values, such as speed, range of motion, muscle activation, etc. being below a predefined threshold value), injury (e.g., during a workout), distress, heart rate above a predefined threshold, etc. The one or more predefined recipient conditions can be detected based on live video data associated with the recipient (e.g., gathered via the smart mirror and/or the mobile compute device), sensor data gathered by one or more wearable electronic accessories (e.g., received at the smart mirror and/or the mobile compute device), etc.

In some embodiments, an instructor provides input to his/her smart mirror and/or mobile compute device (e.g., via voice, video gesturing, touch interaction with a graphical user interface, etc.) to cause display, within a display panel or GUI of a plurality of smart mirrors and/or mobile compute devices of a subset of workout participants, a request or suggestion for the subset of workout participants to send encouragement messages to at least one other workout participant not included in the subset of workout participants.

In some embodiments, encouragement messages received for a given recipient user of a smart mirror can be stored (e.g., in memory of the smart mirror and/or in a memory of a cloud server or other remote compute device communicably coupled with the smart mirror, app and/or mobile compute device of the user), as "encouragement data," and tracked over time. The encouragement data can be compared to other real-time and/or stored data associated with the user, such as sensor data, workout performance data, workout data (e.g., type, intensity, instructor, number of participants, targeted muscle groups, etc.), social media data, biometric data, etc. to determine the effectiveness of the (historical) encouragement messages. Based on the determined effectiveness of the historical encouragement messages, the smart mirror and/or app (optionally using one or more artificial intelligence (AI) (e.g., machine learning) algorithms) can determine encouragement message types and/or encouragement message delivery timing that are deemed to be most effective in helping/encouraging the recipient user.

Challenge ("Face-Off") Workouts

In some embodiments, a first user of a first smart mirror in a first location can send a "challenge" request (e.g., by interacting with a GUI of the first smart mirror or by interacting with a GUI of a first mobile compute device of the first user) to a second user of a second smart mirror in a second location (the second smart mirror being different from the first smart mirror and the first location being different from the second location). The challenge request is then displayed via a GUI of the second smart mirror (and/or via a GUI of a second mobile compute device of the second user), and the second user can accept or deny the challenge request via the same GUI(s). If the second user denies the challenge request, a "denied" response is sent back to the first smart mirror and/or the first mobile compute device. If the second user accepts the challenge request, an "accepted" response is sent back to the first smart mirror and/or the first mobile compute device, and a challenge workout (e.g., selected by the first user, as part of the challenge request generation) is simultaneously or substantially simultaneously displayed via both the first smart mirror and the second smart mirror, optionally at a mutually agreed later time.

During the challenge workout, video of the first user, obtained via one or more video cameras of the first smart mirror and/or via camera(s) of the first mobile compute device, and/or audio of the first user, obtained via one or more microphones of the first smart mirror and/or via microphone(s) first mobile compute device, are live streamed to the second smart mirror and displayed via the display panel of the second smart mirror. Similarly, during the challenge workout, video of the second user, obtained via one or more video cameras of the second smart mirror, and/or audio of the first user, obtained via one or more microphones of the first smart mirror, are live streamed to the first smart mirror and displayed via the display panel of the first smart mirror. As such, during the challenge workout, the first user and the second user can see themselves and their challenger (i.e., the other user) in their respective smart mirrors. Also during the workout, each of the first smart mirror and the second smart mirror (e.g., via the app running on the smart mirror) can: analyze and/or record video of the first user, analyze and/or record video of the second user, receive (and, optionally, analyze) biometric data from one or more wearable electronic accessories of the first user, and/or receive (and, optionally, analyze) biometric data from one or more wearable electronic accessories of the second user, to determine scores for the first user and the second user, and to identify a winner of the challenge workout based on the scores. In some embodiments, the scores can include numeric values that are associated with, or calculated based on, the biometric data, but that do not include the biometric data itself. For example, a heartrate within a first range may be assigned a score of "1," whereas a heartrate within a second range may be assigned a score of "2." In other embodiments, the scores can include non-numeric values (e.g., letters, characters, symbols, graphics, images, etc.). For example, a breathing rate within a first range may be assigned a score of "A," whereas a breathing rate within a second range may be assigned a score of "B." The winner of the challenge workout can be displayed (as text, image(s) and/or audio output) via a GUI of the first smart mirror (and/or the first mobile compute device), displayed (as text, image(s) and/or audio output) via the second smart mirror (and/or the first mobile compute device), and saved in at least one memory (e.g., of the first smart mirror, the second smart mirror, a cloud-based server or other remote server, etc.) for later retrieval and viewing.

In other embodiments, a first user and a second user of a common (single) smart mirror in common (single) location can select a challenge workout (e.g., by interacting with a GUI of the first smart mirror or by interacting with a GUI of a first mobile compute device of the first user). In response to selecting the challenge workout, the smart mirror displays a challenge workout (e.g., selected by the first user and/or the second user, as part of the challenge workout selection). During the challenge workout, live video of the first user and the second user, obtained via one or more video cameras of the smart mirror, is displayed via the smart mirror display panel.

In other embodiments, a user of a smart mirror in a given location can select a challenge workout (e.g., by interacting with a GUI of the smart mirror or by interacting with a GUI of a mobile compute device of the user), where the challenge workout includes a previously-recorded video of the user performing a desired workout (and, optionally, including an overlay of numeric and/or non-numeric scores calculated at the time of the previous recording). In response to selecting the challenge workout, the smart mirror displays ("replays") the challenge workout, such that the user can "face off" against his/her own previous performance of the workout. During the challenge workout, live video of the user, obtained via one or more video cameras of the smart mirror, is displayed via the smart mirror display panel, along with the challenge workout (with optional score overlay(s)) and, optionally, with an additional overlay of numeric and/or non-numeric scores based on the user's performance during the replay of the challenge workout. For example, in some such embodiments, the user can view both his/her score(s) from the previously-recorded video and his/her score(s) calculated during the replay, so that he/she can compare them and be motivated by them. The score(s) may change over time, throughout the duration of the challenge workout. In some embodiments, rather than displaying the scores from the previously-recorded video and the scores calculated during the replay individually, a numeric or non-numeric representation of the difference between the scores from the previously-recorded video and the scores calculated during the replay may be generated and displayed (e.g., a graphic, such as a thermometer, that shows a user (for example, via a color of the graphic, a length of the graphic, etc.) whether he/she is performing better or worse than he/she did during the previously-recorded workout, at any given time). In other words, the graphic can represent the user's "relative" performance, as compared with the previously-recorded workout.

In still other embodiments, a first user of a first smart mirror in a first location and a second user of a second smart mirror in a second location (the second smart mirror being different from the first smart mirror and the first location being different from the second location) can be selected automatically (referred to herein as a "face-off pairing"), by the app, based on a competitive compatibility score generated using a competitive compatibility algorithm. The competitive compatibility algorithm can use some or all of the following data to determine face-off pairings: historical biometric data, current biometric data, historical sensor data, current sensor data, historical workouts, historical workout performance, current workout and exercise, user preferences, and user demographics. Upon automatic selection of a face-off pairing, the app can send challenge requests to the smart mirror(s) of the first user and the second user, for display via a GUI thereof, such that the first user and the second user can accept or deny the challenge request. If both the first user and the second user (if associated with different smart mirrors in different locations) or one of the first user or the second user (if associated with the same common smart mirror) accept the challenge request, a challenge workout (e.g., selected by the app, optionally also based on the competitive compatibility algorithm) is displayed, via both smart mirrors simultaneously, or via the common smart mirror, respectively.

In some embodiments, the app uses AI to automatically identify face-off pairings that are predicted to promote increased future user engagement. For example, AI can be used to target predefined outcomes, by selecting a specified user having a higher predicted likelihood of winning certain challenges, and/or by selecting a specified user having a higher predicted likelihood of losing certain challenges. In some such embodiments, AI may select face-off pairings such that a user that has been exercising less frequently is predicted to lose automatically identified face-off pairings more frequently, and/or such that a user that has been exercising more frequently is predicted to win automatically identified face-off pairings more frequently.

In some embodiments, a networked plurality of smart mirrors can be configured (e.g., via a shared app, optionally also running on one or more mobile compute devices of users of the smart mirrors) to host a ladder tournament competition including a plurality of face-off pairings. Each face-off pairing can be broadcast via the networked plurality of smart mirrors to spectator users, participant users, and/or competitor users within the tournament (e.g., who have signed up for the tournament via the app). The app can automatically update a user listing within a ladder (which may be displayed in each mirror of the networked plurality of mirrors) in real-time or at a various times as the ladder tournament progresses.

In some embodiments, face-off pairings can be between two "teams" of smart mirror users, with each team including two or more competitors. During the face-off workouts, each team member within a given face-off pairing can view, via his/her smart mirror, the video and/or performance metrics (e.g., scores) of the other three team members, as well as the current point totals for each team. The teams can compete with each other in parallel or in series.

In some embodiments, face-off pairings of individual users can be implemented in a "tag team" format, such that a first user competes with a second user one-on-one, and when one of the users (e.g., the second user) tires out, a third user (e.g., viewing the face-off workout) can "tag" in and take the place of the second user, to continue the tag team face-off workout (with the third user's being captured by the smart mirror of the third user and displayed via the smart mirror of the first user) in a continuous manner. Similarly, face-off pairings of individual users can be implemented in a "relay race" format, such that a first user competes with a second user one-on-one, and when each of the first user and the second user reaches a particular/predetermined stage (e.g., distance, time, etc.), a third user and a fourth user, take over for the first user and the second user, respectively, to continue the relay face-off workout in a continuous manner.

In-Workout Spotlights:

In some embodiments, a plurality of users, each with his/her own smart mirror, participates, in parallel, in a common workout presented via their smart mirrors. During the workout, a "spotlight" display (e.g., including text, graphics, images and/or animation) can be applied to or associated with one or more selected users, and the spotlight display can be presented (e.g., as an overlay on a representation of the selected user(s)), via the smart mirrors of the participant users. The spotlight display can be transient (e.g., configured to be displayed for a predetermined period of time). The user(s) selected to be "spotlighted" can be selected automatically (e.g., by the app, using an algorithm, rule(s) and/or schedule) or can be selected by one or more of the participant users. For example, a user who is celebrating a birthday on the day of the workout can be automatically chosen for a spotlight, in response to determining (e.g., based on a calendar) that it is his/her birthday.

In some embodiments, a spotlight display is generated, selected and/or displayed (e.g., by a smart mirror, an app running on the smart mirror, a remote server communicably coupled to the smart mirror, a mobile compute device communicably coupled to the smart mirror, and/or an app running on the mobile compute device) using one or more AI algorithms. For example, an AI algorithm can identify, e.g., based on biometric data of one or more users from the plurality of users collected within a predefined period of time, one or more users from the plurality of users that are determined to need, or to be most in need of, encouragement, inspiration, or motivation (e.g., based on a detected decline in intensity, power, etc.). In some such embodiments, where more than a predetermined threshold number of users from the plurality of users are identified as needing encouragement, the AI algorithm and/or the app can down-select a subgroup of users from those identified as needing encouragement, such that spotlight displays are only displayed for those users within the subgroup (e.g., to avoid visually crowding/overwhelming the display, diluting the message, etc.). Similarly and more generally, in other embodiments, where more than a predetermined threshold number of users from the plurality of users are identified as candidates to be "spotlighted," for example because they have birthdays or anniversaries, the AI algorithm and/or the app can down-select a subgroup of users from those candidates, such that spotlight displays are only displayed for those users within the subgroup (e.g., to avoid visually crowding/overwhelming the display, diluting the message, etc.).

Friending

In some embodiments, a first user of a first smart mirror can "invite" at least a second user of a second smart mirror to become a friend via a "double-opt-in" process (i.e., both the first user and the second user agree to friend each other). A number of "friends" of the first user who have previously completed a workout or attended a class, or who are actively participating in an ongoing instance of the workout, may be displayed and/or highlighted (optionally with prioritization) within the GUI of the given user's smart mirror during the workout or prior to the workout. Alternatively or in addition, live video of one or more friends of the first user may be displayed and/or highlighted (optionally with prioritization) during the workout, and/or icons, images, text, or other representations of the one or more friends of the first user may be displayed and/or highlighted (optionally with prioritization) during the workout.

In some embodiments, a smart mirror of a first user displays (e.g., during a workout) an activity feed that is viewable by the first user and, optionally, by friends of the first user (e.g., via their respective smart mirror). The activity feed can include data associated with the first user and with friends of the first user, including (but not limited to) one or more of: name, username, location, online status, workout log, biometric data (e.g., heart rate data), images, videos, accomplishments, milestones, etc. A first user may interact with an activity feed of a friended user, e.g., by posting text, emojis, videos, images, etc. in the activity feed.

In some embodiments, a smart mirror of a first user displays (e.g., during a workout) a leaderboard of all friended users, a subset of friended users, or users from the entire networked smart mirror community. Positioning of users within the leaderboard can be based on any or all of the following metrics: workouts completed, biometric data (e.g., heart rate data), points earned during competitive (e.g., "challenge") workouts, and values calculated based on the foregoing data (e.g., most improved user(s)). The leaderboard can include a "podium" section (e.g., at the top of the leaderboard) that includes a predefined number (e.g., two, three, four, or five) of the highest-ranked users.

Trending Workouts

In some embodiments, workouts that are "trending" in a predefined community or subset of the community (e.g., a subset of the community that includes users similar to a first user) can be displayed via a smart mirror to the first user. As used herein, "trending" can refer to the condition of having a high overall rating, a high recent rating (e.g., within a predefined preceding period of time), a high overall usage, a high recent usage (e.g., within a predefined preceding period of time), etc. Trends can be defined and/or identified using one or more AI algorithms. For example, AI can be used to determine a desirable time window over which to identify trends (e.g., day, week, month, season) and/or a desirable geographic region within which to identify trends (e.g., country, state, county, city) and/or a desirable subset of users among which to identify trends (e.g., demographics, fitness level, workout frequency, user preferences, user settings, friends, etc.), such that a predicted level of user engagement resulting from the trending displays is higher/highest. Trends can be associated with a particular exercise type (e.g., yoga, running, boxing).

Milestones

In some embodiments, a plurality of users, each with his/her own smart mirror, participates, in parallel, in a common workout presented via their smart mirrors. During, before and/or after the workout, one or more "milestones" (e.g., notable events) can be displayed or otherwise presented via one or more smart mirrors (e.g., as text, audio, video, graphics, images, GIFs, etc.). A milestone can be identified (e.g., by a server, by one or more of the smart mirrors, an app running on one or more of the smart mirrors and/or an app running on one or more mobile compute devices) based, for example, on one or more of: class performance (e.g., based on data gathered during a workout, such as video data and biometric data), exercise performance (e.g., based on data gathered while performing the exercise, such as video data and biometric data), class attendance, performance across workouts (e.g., based on data gathered during a workout, such as video data and biometric data), calendar events (e.g., anniversary of signing up via the smart mirror, birthday, friend anniversaries), and smart mirror community or social interactions. Milestones can be displayed according to a predefined schedule, and thus may expected by the user(s). Alternatively, milestones can be surprise and/or unexpected achievements, such that the user(s) are not expecting to see them. AI can be used to determine one of the following, with regard to milestones: time(s)/date(s) for presenting surprise achievement milestones having the highest predicted likelihood of promoting/triggering future user engagement, types of surprise achievement milestones predicted to "delight" or be welcomed by a particular user, timing of the presentation of surprise achievement milestones during a workout, such that the user has a favorable response (rather than a negative response) to the milestone, a maximum frequency at which milestones may be displayed, such that a predicted likelihood of promoting/triggering future user engagement is highest, etc.

Virtual "Locker Room" Sessions

In some embodiments, a smart mirror app is configured to simulate an interactive "locker room" environment before and/or after a workout. FIG. 4 is a diagram showing an example locker room implementation, in accordance with some embodiments. As shown in FIG. 4, during a first time interval (Time Interval 1—first virtual locker room), users A, E, and F are active (e.g., they are in front of their respective smart mirrors, optionally with their video cameras on, or have their app open on their mobile compute device(s)). At least a subset of the users A, E, and F may plan to participate in a common scheduled workout (which can be either a "live" workout or an "encore" workout). The first time interval precedes the time at which the workout is scheduled to begin. During the first time interval, the users A, E, and F can see and communicate with each other via voice, video, and/or chat (e.g., including text, image, emojis, GIFs (e.g., virtual towel snap GIF), etc.). Also during the first time interval, one or more user-selected backgrounds (e.g., images uploaded by each user or by a user that organized the workout) and/or images selected by the smart mirror app (e.g., according to one or more predefined rules and/or algorithms) can be displayed within the smart mirror of each of users A, E, and F. Images selected by the smart mirror app can include, for example, images of products for promotion and/or images depicting the rendering of services for promotion. The selection of images of products for promotion and/or images depicting the rendering of services for promotion can be based on one or more rules and/or algorithms based, for example, on user demographics, user preferences, user location data, user purchase history, etc. From the point of view of, for example, user A, other active users E and F can be "seen" via live video stream and/or via other representations, such as avatars, images, text, etc. In some embodiments, the visual/displayed appearance (e.g., including the background) of the first virtual locker room automatically changes as different users talk (e.g., concurrent with the current speaker being featured/enlarged within the viewable area). In some embodiments, an animation is displayed, to participants of the first virtual locker room and during the first time interval, of people getting ready for a workout (e.g., putting on shoes, warming up, etc.).

During a second time interval (Time Interval 2—scheduled workout), an instructor 401 and users A, B, C, and F are active (e.g., they are in front of their respective smart mirrors, optionally with their video cameras on). During a third time interval (Time Interval 3—second virtual locker room), users D, B, and F are active (e.g., they are in front of their respective smart mirrors, optionally with their video cameras on, or have their app open on their mobile compute device(s)). Users B and F participated in the preceding workout (during the second time interval), whereas user D did not. During the third time interval (similar to during the first time interval), the users B, D, and F can see and communicate with each other via voice, video, and/or chat (e.g., including text, image, emojis, GIFs (e.g., virtual towel snap GIF), etc.). Also during the third time interval, a user-selected background (e.g., an image uploaded by each user) can be displayed within the smart mirror of each of users A, E, and F. From the point of view of, for example, user B, other active users D and F can be "seen" via live video stream and/or via other representations, such as avatars, images, text, etc. In some embodiments, the visual/displayed appearance (e.g., including the background) of the first virtual locker room automatically changes as different users talk (e.g., concurrent with the current speaker being featured/enlarged within the viewable area). In some embodiments, an animation is displayed, to participants of the second virtual locker room and during the third time interval, of people doing post-workout activities (e.g., taking off shoes, cooling down, etc.).

In some embodiments, during the first virtual locker room and/or the second virtual locker room, the smart mirror displays of all participants are synchronized such that they display the same events occurring at the same time (e.g., users entering and exiting the virtual locker room). For example, if three users are in the virtual locker room, and a fourth user enters the locker room, the three users can simultaneously view that fourth user entering. As the fourth user enters, he/she sees the three friends already there in the virtual locker room.

Figure 4A:
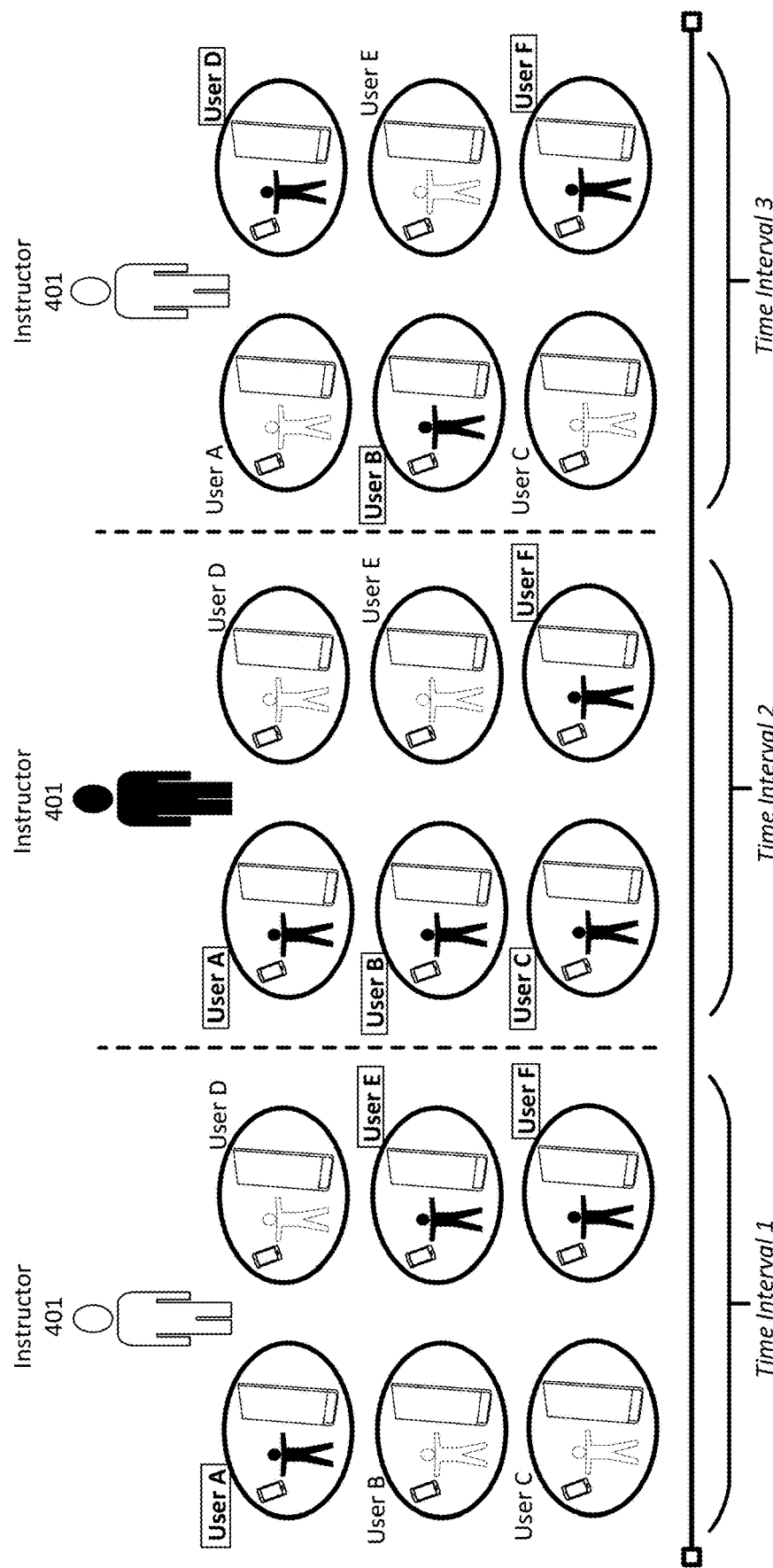
FIG. 4A is a diagram showing an example locker room implementation, in accordance with some embodiments.
Figure 4B:
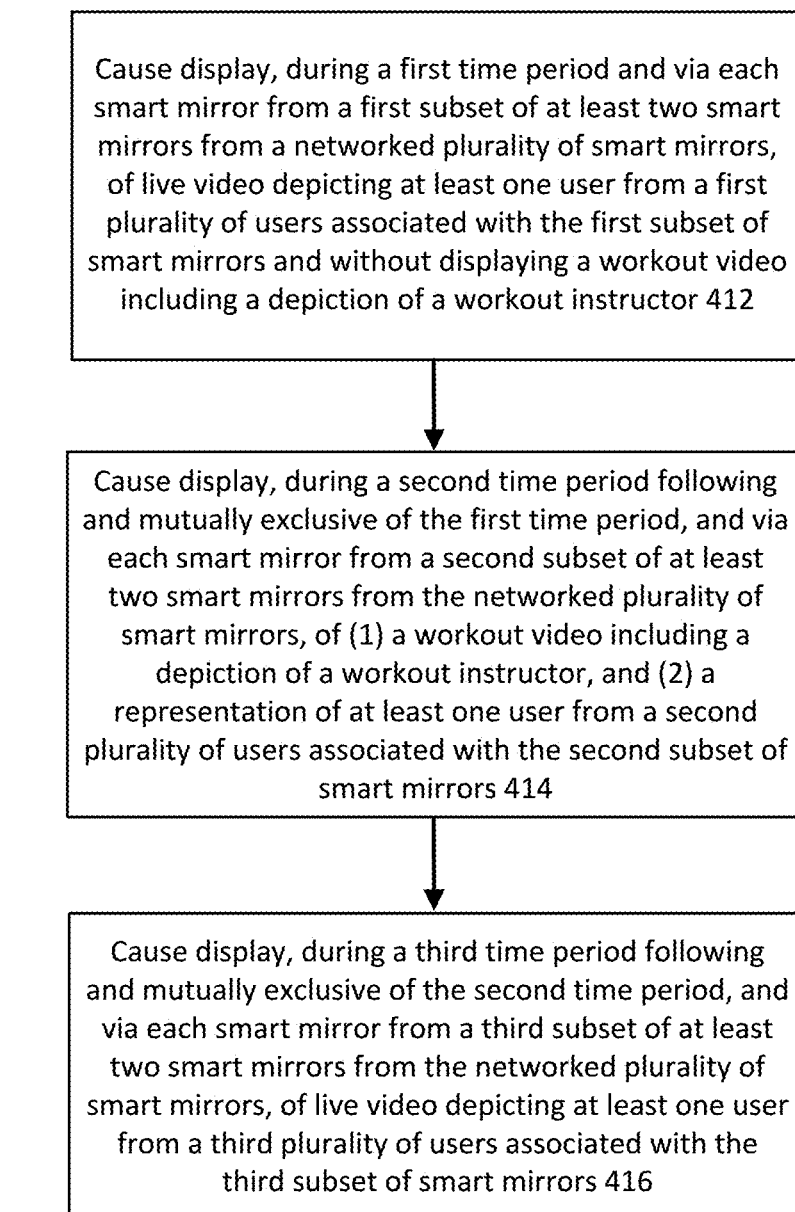
FIG. 4B is a flow diagram of an example method of hosting a locker room session within a smart mirror network, in accordance with some embodiments.

FIG. 4B is a flow diagram of an example method of hosting a locker room session within a smart mirror network, in accordance with some embodiments. As shown in FIG. 4B, the method 410 of hosting a locker room session within a smart mirror network includes, at 412, causing display, during a first time period and via each smart mirror from a first subset of at least two smart mirrors from a networked plurality of smart mirrors, of live video depicting at least one user from a first plurality of users associated with the first subset of smart mirrors, without displaying a workout video including a depiction of a workout instructor and without displaying any video from the smart mirrors outside of the first subset of smart mirrors. The method 410 optionally also includes causing display, during the first time period and via each smart mirror from the first subset of smart mirrors from the networked plurality of smart mirrors, of at least one user-selected background and/or of at least one background automatically selected by a software application associated with the first subset of smart mirrors. In some embodiments, the at least one user-selected background and/or automatically selected background (collectively, "background(s)") can have a black appearance, a single-color appearance, or a white appearance that is substantially uniform. In other embodiments, the background(s) can have a "locker room" type appearance (e.g., an interior of a locker room), which may include graphics or other representations of any of the following non-exhaustive list of items: lockers, doors, tile flooring, carpeting, benches, towels, water bottles, water fountains, shoes, clothing, hangers, hampers, hair dryers, scales, waste baskets, free weights, bulletin boards with notifications, etc. In still other embodiments, the background(s) can include an animation or sequence of images.

Any of the foregoing background(s) can further include an identifier of the associated user, which may include text, a photograph, an avatar, etc. Alternatively or in addition, the background(s) can include a depiction of a natural environment (e.g., terrain). Alternatively or in addition, the background(s) can include a depiction of at least one product for promotion. The at least one product can be selected (e.g., by a software app, the smart mirror, or a remote server) based on a workout type associated with the workout video. Optionally, the depiction of the at least one product for promotion can be interactive (e.g., hyperlinked or otherwise functionalized) such that if a user interacts with the depiction of the at least one product for promotion, the user may be "redirected" via the user's smart mirror (or other compute device in communication with that user's smart mirror, such as a smartphone) for purchase of the at least one product, or a representation of the at least product may be added to a digital/electronic shopping cart for subsequent purchase. The digital/electronic shopping cart may be stored at the user's smart mirror, sent to and stored at a remote server, and/or sent to and stored at a compute device of the user.

The method 410 also includes causing display, at 414, during a second time period following and mutually exclusive of the first time period, and via each smart mirror from a second subset of at least two smart mirrors from the networked plurality of smart mirrors, of: (1) a workout video including a depiction of a workout instructor, and (2) a representation of at least one user from a second plurality of users associated with the second subset of smart mirrors.

The method 410 also includes causing display, at 416, during a third time period following and mutually exclusive of the second time period, and via each smart mirror from a third subset of at least two smart mirrors from the networked plurality of smart mirrors, of live video depicting at least one user from a third plurality of users associated with the third subset of smart mirrors. The second time period can follow the first time period without an intervening time period, and/or the third time period can follow the second time period without an intervening time period. The method 410 optionally also includes causing display, during the third time period and via each smart mirror from the first subset of smart mirrors from the networked plurality of smart mirrors, of at least one user-selected background and/or of at least one background automatically selected by a software application associated with the first subset of smart mirrors. The at least one user-selected background and/or automatically selected background (collectively, "background(s)") can have a "locker room" type appearance (e.g., an interior of a locker room), which may include graphics or other representations of any of the following non-exhaustive list of items: lockers, doors, tile flooring, carpeting, benches, towels, water bottles, water fountains, shoes, clothing, hangers, hampers, hair dryers, scales, waste baskets, free weights, etc. Alternatively or in addition, the background(s) can include an identifier of the associated user, which may include text, a photograph, an avatar, etc. (optionally in lieu of providing video of that user) Alternatively or in addition, the background(s) can include a depiction of a natural environment (e.g., terrain). Alternatively or in addition, the background(s) can include a depiction of at least one product for promotion. The at least one product can be selected (e.g., by a software app, the smart mirror, or a remote server) based on a workout type associated with the workout video. Optionally, the depiction of the at least one product for promotion can be interactive (e.g., hyperlinked or otherwise functionalized) such that if a user interacts with the depiction of the at least one product for promotion, the user may be "redirected" via the user's smart mirror (or other compute device in communication with that user's smart mirror, such as a smartphone) for purchase of the at least one product, or a representation of the at least product may be added to a digital/electronic shopping cart for subsequent purchase. The digital/electronic shopping cart may be stored at the user's smart mirror, sent to and stored at a remote server, and/or sent to and stored at a compute device of the user.

In some embodiments, the background(s) displayed during the first time period is the same as the background(s) displayed during the third time period. In other embodiments, the background(s) displayed during the first time period is different from the background(s) displayed during the third time period.

In some embodiments, the first subset of smart mirrors and/or the third subset of smart mirrors is configured such that users from the first plurality of users and/or users from the third plurality of users can communicate with one another during the first time period via at least one of: voice, video, text, emojis, animation, or imagery.

In some embodiments, the method 410 also includes modifying an appearance of the live video during the first time period and/or during the third time period, in response to detecting that one of the users from the first plurality of users is speaking.

In some embodiments, the first plurality of users and the second plurality of users have at least one user in common, and/or the second plurality of users and the third plurality of users have at least one user in common, and/or the first plurality of users and the third plurality of users have at least one user in common.

FIG. 4C is a flow diagram of an example method of hosting a locker room session on networked compute devices (which may include a combination of smart mirrors and mobile compute devices such as smartphones, for a variety of users), in accordance with some embodiments. As shown in FIG. 4C, the method 420 includes causing display, at 422, during a first time period and via each compute device from a first subset of at least two compute devices from a networked plurality of compute devices, of live video depicting at least one user from a first plurality of users associated with the first subset of compute devices, without displaying a workout video including a depiction of a workout instructor and without displaying video of users outside of the first plurality of users. The networked plurality of compute devices includes at least one smart mirror and at least one mobile communication device.

The method 420 also includes, at 424, causing display, during a second time period following and mutually exclusive of the first time period, and via each compute device from a second subset of at least two compute devices from the networked plurality of compute devices, of (1) a workout video including a depiction of a workout instructor, and (2) a representation of at least one user from a second plurality of users associated with the second subset of compute devices The method 420 also includes, at 426, causing display, during a third time period following and mutually exclusive of the second time period, and via each compute device from a third subset of at least two compute devices from the networked plurality of compute devices, of live video depicting at least one user from a third plurality of users associated with the third subset of compute devices, without displaying a video of the workout instructor or any compute device outside the third plurality of compute devices.

In some embodiments, the second time period follows the first time period without an intervening time period, and/or the third time period follows the second time period without an intervening time period.

In some embodiments, the first subset of compute devices and the second subset of compute devices have at least one compute device in common and/or the second subset of compute devices and the third subset of compute devices have at least one compute device in common and/or the first subset of compute devices and the third subset of compute devices have at least one compute device in common.

In some embodiments, each of the first subset of compute devices, the second subset of compute devices, and the third subset of compute devices includes a combination of at least one smart mirror and at least one mobile compute device such as a smartphone, for multiple different users.

In some embodiments, at least one of the first subset of compute devices or the third subset of compute devices is configured such that users from the first plurality of users and/or users from the third plurality of users can communicate with one another during the first time period and/or during the third time period via at least one of: voice, video, text, emojis, animation, or imagery. The voice, text, emojis, animation, or imagery can optionally be presented/output in lieu of a video representation of one or more users from the first plurality of users and/or the third plurality of users. In some embodiments, live video can be streamed from a remote compute device (e.g., a compute device at a broadcast studio and/or a compute device of a non-user (i.e., a person not included in the first plurality of users and/or the third plurality of users)) to compute device(s) of one or more users from the first plurality of users during the first time period and/or to compute device(s) of one or more users from the third plurality of users during the third time period, for display thereon. For example, the live video can include video of a guest speaker (e.g., a trainer, a nutritionist, etc.) and can be streamed substantially in real time as part of a question-and-answer session, such that the one or more users from the first plurality of users and/or the one or more users from the third plurality of users can ask questions (e.g., by sending one or more of live video data, pre-recorded video data, live audio data, pre-recorded video data, or text data to the remote compute device) of the guest speaker and view the replies given by the guest speaker via the live video stream when displayed.

In some embodiments, the method 420 also includes causing display, during the first time period and via each compute device from the first subset of compute devices from the networked plurality of compute devices, of at least one user-selected background and/or at least one background automatically selected by a software application (collectively, "background(s)," as discussed above with reference to FIG. 4B). The at least one user-selected background can include a depiction of at least one product for promotion, a depiction of an interior of a locker room, and/or at least one announcement. Similarly, the method 420 can include causing display, during the third time period and via each compute device from the third subset of compute devices from the networked plurality of compute devices, of at least one user-selected background and/or at least one background automatically selected by a software application (collectively, "background(s)").

In some embodiments, the method 420 also includes modifying an appearance of the live video during the first time period, in response to detecting that one of the users from the first plurality of users is speaking. Modifying the appearance of the live video can include one or more of: increasing a size of a representation of the user that is speaking, increasing a prominence of the representation of the user that is speaking, adding a halo-effect, highlight, or other border around the representation of the user that is speaking (e.g., around a displayed video tile), changing a color of the representation of the user that is speaking, changing a font of the representation of the user that is speaking, changing a contrast of the representation of the user that is speaking, increasing a volume level associated with the user that is speaking (and/or decreasing a volume level associated with non-speaking users), changing a brightness level of the representation of the user that is speaking, etc.

In some embodiments, the first plurality of users and the second plurality of users have at least one user in common. Alternatively or in addition, the second plurality of users and the third plurality of users can have at least one user in common. Alternatively or in addition, the first plurality of users and the third plurality of users can have at least one user in common.

In some embodiments, a method of hosting a locker room session includes causing display, during at least one of a first time period or a third time period, and via each compute device from a first group of at least two compute devices from a networked plurality of compute devices, of a representation of at least one user from a first plurality of users associated with the first group of compute devices, without displaying a workout video including a depiction of a workout instructor. The networked plurality of compute devices includes at least one smart mirror and at least one mobile communication device. The method also includes causing display, during a second time period and via each compute device from a second group of at least two compute devices from the networked plurality of compute devices, of: (1) a workout video including a depiction of a workout instructor, and (2) a representation of at least one user from a second plurality of users associated with the second group of compute devices, the second time period following and mutually exclusive of the first time period, and the third time period following and mutually exclusive of the second time period.

In some embodiments, at least one of the representation of the at least one user from the first plurality of users or the representation of the at least one user from the second plurality of users includes one of live video or an avatar.

In some embodiments, at least one of the representation of the at least one user from the first plurality of users or the representation of the at least one user from the second plurality of users includes a user-selected avatar.

In some embodiments, the workout video is a first workout video, each user from the first plurality of users at least one of: associated with a common friend group, registered to view the first workout video during the second time period, or registered to view, during the second time period, a second workout video different from the first workout video.

In some embodiments, the method also includes ceasing display of the representation of the at least one user from the first plurality of users when the at least one of the first time period or the third time period has ended.

In some embodiments, the method also includes causing display, during the at least one of the first time period or the third time period, and via a subset of compute devices from the first group of at least two compute devices, of a representation of at least two users from a subset of users from the first plurality of users, without displaying a workout video including a depiction of a workout instructor and without displaying a representation of any remaining user from the subset of users from the first plurality of users.

In some embodiments, each user from the first plurality of users is associated with a common friend group, and the method also includes (1) causing a message representing an invitation to be sent to an additional user not associated with the friend group in response to a request from a user from the first plurality of users, and (2) causing display, during the at least one of the first time period or the third time period, of a representation of the additional user in response to the additional user accepting the invitation.

Although described in FIG. 4B as including at least two smart mirrors, in other embodiments, the first subset, the second subset and/or the third subset can include at least three smart mirrors or at least four smart mirrors. Similarly, although described in FIG. 4C as including at least two compute devices, in other embodiments, the first subset, the second subset and/or the third subset can include at least three compute devices or at least four compute devices.

Figure 4E:
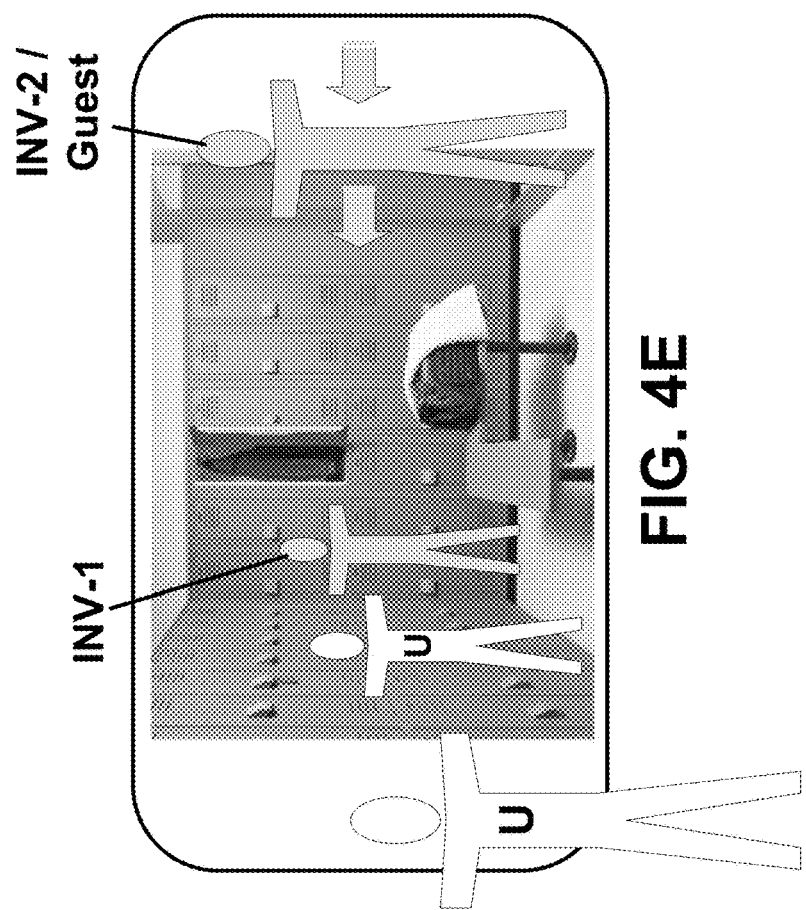
FIGS. 4D-4E show example display configurations for a locker room session, in accordance with some embodiments.
Figure 4D:
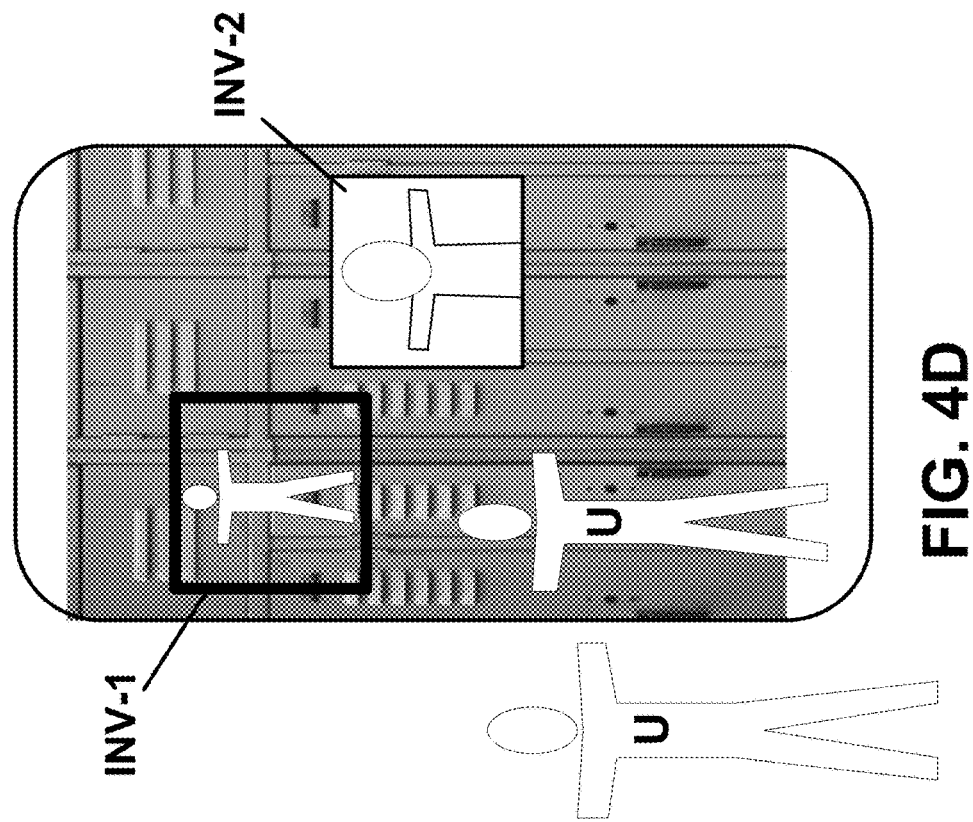

FIGS. 4D-4E show example display configurations for a locker room session, in accordance with some embodiments. As shown in FIG. 4D, a locker room environment can be displayed in a vertical/"portrait" orientation, within a smart mirror display and/or within a GUI of a mobile device (e.g., a smartphone), and can be presented as a background that appears behind other objects within the viewable area. Also shown in FIG. 4D is a user "U" and a representation of the user "U" within the display. The representation of the user "U" within the display can be a reflected image (e.g., via a smart mirror) of the user, a still image of the user, a live video of the user, or a pre-recorded video image of the user. Also shown in FIG. 4D are representations of invitees "INV-1" and "INV-2," presented separately, in discrete panes arranged within the display area. The invitees "INV-1" and "INV-2" may be geographically remote from user U. The representations of invitees "INV-1" and "INV-2" may include panes with borders or without borders. The representations of invitees "INV-1" and "INV-2" may include their own associated backgrounds (e.g., "virtual" backgrounds, backgrounds selected by the associated user, backgrounds automatically selected by the associated compute device(s), etc.) or may be presented without their own associated backgrounds, such that the locker room background is visible surrounding the depictions of the invitees. The representations of invitees "INV-1" and "INV-2" may include still imagery, live video, or pre-recorded video of the invitees, at any of a variety of aspect ratios and levels of zoom (e.g., such that the invitee's full body appears within the associated representation, or only a portion of the invitee's body appears within the associated representation).

FIG. 4E shows a locker room environment that is displayed in a landscape orientation, within a smart mirror display and/or within a GUI of a mobile device (e.g., a smartphone), and similar to the locker room environment of FIG. 4D, can be presented as a background that appears behind other objects within the viewable area. Also shown in FIG. 4E is a user "U" and a representation of the user "U" within the display. The representation of the user "U" within the display can be a reflected image (e.g., via a smart mirror) of the user, a still image of the user, a live video of the user, or a pre-recorded video image of the user. In some embodiments, where the representation of the user U within the display of user U is a reflected image, the smart mirrors and/or mobile devices of other locker room participants (i.e., the invitees and/or guests) can display live video imagery of user U as captured by the camera of the smart mirror of user U, the still image of the user, or the pre-recorded video image of the user U. Similarly, in embodiments where the representation of the user U within the display of user U is a still image of the user, a live video of the user, or a pre-recorded video image of the user, the smart mirrors and/or mobile devices of other locker room participants (i.e., the invitees and/or guests) can display live video imagery of user U as captured by the camera of the smart mirror of user U, the still image of the user, or the pre-recorded video image of the user U.

In some embodiments (not shown), the smart mirror is configured such that, when a locker room environment is displayed and the user U is using the smart mirror, the user U is unable to see his/her own reflection in the mirror (e.g., the reflective feature is reduced or eliminated), thereby simulating an in-person locker room setting. The reflective feature of the smart mirror can be reduced, for example, by one or more of: digital compensation within the smart mirror display based on live video imagery captured by the camera of the smart mirror and/or position data detected by one or more sensors operably coupled to the smart mirror, activation of one or more light sources positioned to direct light onto a back surface or front surface of the smart mirror, or an electronic modification of a surface roughness of the smart mirror such that the reflectivity of the surface of the smart mirror is reduced. In some such embodiments, the locker room environment includes a representation of a simulated mirror (e.g., on a wall next to a set of lockers), and when the camera of the user U's smart mirror or smartphone detects a predefined positioning of the user U, a live video or reflected image of the user U appears in the simulated mirror of the locker room environment but does not appear outside the simulated mirror within the locker room environment. In some embodiments, one or more smart mirror surfaces are manufactured to have a predefined level of transmittance (e.g., between 35% and 85%) and a predefined level of reflectance (e.g., between 65% and 15%) such that the smart mirror surface(s) can appear to be fully reflective, partially reflective, or fully transparent, dependent upon an amount and/or intensity of light that is directed toward the one or more smart mirror surfaces.

In some embodiments (not shown), the smart mirror and/or a mobile compute device of the user U is configured such that, when a locker room environment is displayed and the user U is using the smart mirror and/or the mobile compute device, no representation of the user U is presented in the display of the smart mirror and/or the mobile compute device of the user U. In other words, no live video, avatar, or other representation of the user U is presented to the user U via the smart mirror and/or the mobile compute device, however one or more representations of the user U may be presented to some or all of the other invitees/participants of the locker room session, via their associated smart mirrors and/or the mobile compute devices.

Also shown in FIG. 4E are representations of invitees "INV-1" and "INV-2/Guest," presented separately, but without any associated panes, arranged within the display area. In other words, the invitees appear to be present in the simulated locker room, in full within the display area, and without their own associated backgrounds or borders (apart from the boundary of the invitees' bodies themselves). The invitees "INV-1" and "INV-2" may, in reality, be geographically remote from user U, but appear adjacent to one another within the locker room display. FIG. 4E also shows lockers, a bench, an open locker door with a jacket hanging inside the locker, a gym bag placed on the bench, and a towel draped over the gym bag. During a locker room session (e.g., as shown and described herein with reference to FIGS. 4B-4C) in which invitee 1 (INV-1) uses live video to transmit his/her image, INV-1 may ambulate and/or talk. When INV-1 ambulates and/or talks, INV-1 will appear (either concurrently or after a delay), to the user U and to INV-2, to be ambulating and/or talking within the locker room environment.

In some embodiments, during a locker room session, a subset of invitees/participants that are actively engaged in discussion (e.g., as determined based on one or more microphone voice detection, motion detection, and/or speech recognition via the smart mirrors and/or mobile compute devices of the associated users) are moved to and/or presented within a foreground of the simulated locker room, and invitees/participants that are not actively engaged in discussion (e.g., as determined based on one or more microphone voice detection, motion detection, and/or speech recognition via the smart mirrors and/or mobile compute devices of the associated users) are moved to and/or presented within a background of the simulated locker room, or are moved behind the invitees/participants that are in the foreground, or are removed from the visual presentation of the locker room (but optionally still able to listen to and view the locker room session), and may be displayed within the simulated locker room once again upon initiation of voice communication and/or movement. Such reorganization and dynamic down-selection of invitees/participants can result in a less crowded appearance, which can enhance the experience of viewing the locker room session, particularly when on a mobile device.

In some embodiments, a locker room session is accessible only by invitees (and, optionally, a coordinating user), and is not accessible by non-invitees. In other embodiments, a locker room session is initially accessible only by invitees (and, optionally, a coordinating user), and an invitee may invite one or more additional users ("new invitees") to join the in-progress locker room session, for example by sending a push notification to the one or more additional users, or by causing the generation and posting of a social media notification targeting the one or more additional users. Upon acceptance by the one or more additional users of the invitation to join the in-progress locker room session, the one or more additional users may be presented, via a smart mirror and/or mobile device of the one or more additional users, with an interactive graphical feature or weblink via which they can join (e.g., navigate to or cause display of) the in-progress locker room session. In still other embodiments, a locker room session is accessible by any user, without any invitations being sent, without any acceptances being received, and without any invitee status being assigned to any user. Such locker room sessions may be referred to as "waiting room" sessions. During a waiting room session, a representation of each user that joins the waiting room session is displayed via the display(s) of compute devices (e.g., smart mirror(s) and/or mobile compute devices) of each other user that joins the waiting room session during a period of time associated with the waiting room session. A waiting room session may be initiated by one or more users (e.g., by making a selection via, or interacting with, his/her compute device), or may be automatically initiated by a software application associated with a smart mirror or other compute device from a networked plurality of compute devices including the compute devices of the users. The waiting room session may precede in time, or follow in time, a workout session, and the waiting room session may not include the display of workout content depicting an instructor. As described elsewhere herein, users that virtually "congregate" as part of a waiting room session may view depictions of, and/or communicate with, one another using streamed live video, recorded video, voice, text and/or graphical images such as emojis.

In other embodiments, a locker room session is initially accessible only by invitees (and, optionally, a coordinating user), and a non-invitee may submit a request to join the in-progress locker room session. A representation of the request to join may be rendered within the display during the in-progress locker room session, for presentation to one or more of the user U (e.g., the coordinating user) and/or the invitees. One or more of the user U and/or the invitees may accept or decline the request from the non-invitee to join the in-progress locker room session. In some embodiments, acceptance of the request from the non-invitee to join the in-progress locker room session may be completed when only one of the user U or one of the invitees accepts the request. In other embodiments, acceptance of the request from the non-invitee to join the in-progress locker room session is completed when a majority of the current participants in the in-progress locker room session accepts the request. In still other embodiments, acceptance of the request from the non-invitee to join the in-progress locker room session is completed when all of the current participants in the in-progress locker room session accepts the request. In some embodiments, a conflict resolution process may be triggered when two or more current participants in the in-progress locker room session submit conflicting accept/decline indications in response to the request to join.

In some embodiments, live video feeds from locker room session invitees are synchronized during an initialization step and/or iteratively throughout the locker room session. The video synchronization can include aligning timestamps of the live video feeds with one another and/or adjusting a timing relationship between two or more of the live video feeds. The video synchronization can be performed based on one or more header files associated with (e.g., transmitted with) the live video feeds. The video synchronization can be performed at a centralized location (e.g., in a remote server) prior to delivery/distribution of the video feeds to each smart mirrors and/or mobile compute device associated with the locker room session. Alternatively, the video synchronization can be performed at one or more of the smart mirrors and/or mobile compute device associated with the locker room session.

In some embodiments, representations of invitees can vary over the course of the locker room session, switching between live video of the invitees and avatar (or other graphic and/or text based) representations of the invites, in either direction, one or multiple times. The switching between live video and avatar (or vice-versa) can be based on one or more of: predefined invitee preferences, a calculated participation level of the invitee(s), a detected level of movement of the invitee(s), detected gesture(s) of movement of the invitee(s), a detected positioning of the invitee(s) within the field of view of the camera of the invitee(s)'s smart mirror or mobile compute device, etc. For example, when an invitee is not within the field of view of the camera of his/her smart mirror (i.e., is "off-camera"), but had joined the locker room session, an avatar or other representation of that invitee may be displayed via that invitee's smart mirror and/or via smart mirrors and/or mobile compute devices of the other invitees of the locker room session. Subsequently, when that invitee moves into the field of view of the camera of his/her smart mirror (i.e., is "on-camera"), the avatar or other representation of that invitee may cease to be displayed, and instead live video of the invitee may be displayed via that invitee's smart mirror and/or via smart mirrors and/or mobile compute devices of the other invitees of the locker room session. By replacing live video with an avatar during portions of the locker room session, the network traffic associated with the locker room session can be reduced. Alternatively or in addition, a common background can be stored on at least one of a smart mirror or a mobile compute device of each invitee, and can be retrieved locally for display during the locker room session, thereby reducing network traffic.

In some embodiments, a transition display(s) is presented (1) to invitees of a first locker room session that precedes a workout session, during a time period that includes an end portion of the first locker room session and a beginning portion of the workout session, and/or (2) to invitees of a second locker room session that is subsequent to the workout session, during a time period that includes an end portion of the workout session and a beginning portion of the second locker room session. As discussed above, each of the first locker room session and the second locker room session can include the display of an associated plurality of invitees without displaying a workout video depicting an instructor, while the workout session can include display of a workout video depicting an instructor as well as representations of workout participants. The workout participants may include some, none, or all of the invitees of the first locker room, and may include some or all of the invitees of the second locker room. In some embodiments, a first transition display is presented to invitees of a first locker room session that precedes a workout session and a second transition display is presented to invitees of a second locker room session that is subsequent to the workout session. The first transition display can be the same as, or different from, the second transition display. Transition displays can include a digital effect such as one or more of the following: a fade in, a fade out, a wash out, a jump cut, a mix, a cross dissolve, a ripple dissolve, a cutaway, an iris in, an iris out, a crossfade, or a wipe. For example, a transition display can include a linear fade out of the locker room session, a linear fade out of the workout session, a linear fade in of the locker room session, a linear fade in of the workout session.

In some embodiments, invitees of a locker room session can send communications directly to other invitees ("direct communications"), with or without also notifying the other invitees of the locker room session and with or without causing display of the communication to the other invitees of the locker room. The direct communications can include audio, video, text, and/or graphical (non-video) communications. Graphical communications can include animations, graphical images, icons, emojis, sequences of emojis, avatars, or sequences of avatars that are displayed via a display of a smart device and/or mobile compute device of the recipient invitee (and, optionally, other invitees of the locker room session). Examples of graphical communications include, but are not limited to, high-fives, hand claps, passing of virtual objects (e.g., towels, water bottles), etc. Direct communications can be initiated by an invitee in response to that invitee's interaction with a touchscreen of his/her smart mirror or mobile compute device (e.g., a display or GUI thereof), or in response to an audio command spoken by that invitee and detected by a microphone of that invitee's smart mirror or mobile compute device, or in response to a movement (e.g., a gesture) of that invitee detected by a camera or sensor of that invitee's smart mirror or mobile compute device. Similarly, the selection of a type of direct communication and/or the selection of a recipient invitee may be performed by the invitee's interaction with the touchscreen of his/her smart mirror or mobile compute device (e.g., a display or GUI thereof), or in response to an audio command spoken by that invitee and detected by a microphone of that invitee's smart mirror or mobile compute device, or in response to a movement (e.g., a gesture) of that invitee detected by a camera or sensor of that invitee's smart mirror or mobile compute device. In an example embodiment, an invitee may elect to a "towel snap" another invitee ("recipient invitee") via one or more of the foregoing initiation and/or selection techniques discussed above. In response to the invitee's election of the towel snap operation, a towel snap sequence, including an animation, sequence of avatars, or sequence of graphical images, can be triggered for presentation to the recipient invitee (and, optionally, to other invitees of the locker room session) via his/her smart mirror display and/or via his/her mobile compute device GUI. The recipient invitee and optional other invitees of the locker room session may be collectively referred to as the "viewers." The towel snap sequence can include a representation of a rapidly moving towel that is moving along a trajectory and then changing direction back along the same or a similar trajectory (i.e., snapping back). Optionally, the towel snap sequence can include causing an audio snapping noise to play on a speaker of the smart mirror and/or mobile compute device of the recipient invitee (and, optionally, to play on speaker of the smart mirrors and/or mobile compute devices of other invitees of the locker room session), for example coinciding with the display of the changing of direction of the representation of the moving towel. Optionally, the towel snap sequence is performed such that the representation of the moving towel appears to interact with or move toward a representation of the recipient invitee within the display of the viewers.

In some embodiments, the representation of an invitee of a locker room session, when not including live video, may change over the course of the locker room session, and/or may have a first appearance during a first locker room session that precedes a workout session and a second appearance different from the first appearance during a second locker room session that follows (or occurs after) a workout session. For example, an invitee's avatar may have a normal or refreshed appearance during the first locker room session, and may have a tired appearance during the second locker room session (e.g., if that invitee has participated in the intervening workout session). In still other embodiments, an appearance of a representation of an invitee of a locker room session (e.g., of an avatar) may be selected and/or modified in response to one or more detected biometric parameters, such as heart rate, temperature, respiration rate, pulse, etc.

Biometric Connector Systems

In some embodiments, a biometric "connector" apparatus is sized and shaped to connect to, attach to, or be embedded within, at least one of exercise equipment, apparel, footwear (e.g., one shoe or both shoes), or the body of a user, and contains a microcontroller communicably coupled to a plurality of sensors (optionally including at least one "onboard" sensor). The plurality of sensors includes sensors for detecting data that directly measures, or is used in the calculation of, one or more of the following non-exhaustive list of biometric data: position (e.g., via a global positioning system (GPS) sensor, altimeter, etc.), orientation or rotation (e.g., via a gyroscope, magnetometer, etc.), acceleration (e.g., via 3-axis accelerometer(s)), speed/velocity (e.g., limb speed, running speed, etc.), cadence, pace, gait, vibration, muscle activation (i.e., which muscle(s) are being activated, and to what degree) (e.g., using a stretch sensor, vibration sensor, etc.), temperature, humidity, oxygen levels (e.g., blood oxygen level, blood oxygen saturation, etc.), salinity, breathing rate, heart rate (e.g. via a bioimpedance sensor, optical sensor, photoplethysmography (PPS) sensor, etc.), muscle twitch response, heart rate recovery, perspiration rate, intensity, linear force, linear movement, rotational force, rotational movement, power (e.g., running power), repetition counts such as steps (e.g., via a pedometer), range of motion, movement patterns/trajectories, gestures, facial features (e.g., via facial recognition sensors), flexibility, endurance, strength, body fat, and hydration level. A biometric connector apparatus can include a connected weight (or "smart weight"), such as the connected weight 610 of FIG. 6 or the connected weight dumbbell shown in FIG. 7, discussed below.

In some embodiments, a biometric connector system includes one or more biometric connector sensors, each configured to communicate (e.g., via Bluetooth® or other wireless network communications protocol) with one or more smart mirrors. During use (e.g., during a workout), the biometric connector sensor(s) detect biometric data for a user performing the workout, optionally store the biometric data locally (within the biometric connector sensor(s)), and generate and transmit signals representing the biometric data to the smart mirror (and/or to an app running on the smart mirror, and/or to a mobile compute device of the user). Once received, one or more of the following actions can be performed: the biometric data can be stored in memory, a representation of the biometric data (e.g., in text, graphic, and/or audio form) can be presented to the user via the smart mirror and/or via the mobile compute device), an alert can be generated based on the biometric data and presented to the user (e.g., in text, graphic, and/or audio form) via the smart mirror and/or via the mobile compute device), one or more recommendations (e.g., to correct form, to reduce intensity, to begin cool down, to increase intensity, to hydrate, to change to a different workout, etc.) can be generated based on the biometric data (e.g., according to one or more predetermined rules and/or based on one or more algorithms) and presented to the user (e.g., in text, graphic, and/or audio form) via the smart mirror and/or via the mobile compute device), etc.

In some embodiments, a biometric connector system includes one or more biometric connector sensors, each configured to communicate (e.g., via Bluetooth® or other wireless network communications protocol) with one or more smart mirrors (and/or with any other wall-mounted or freestanding appliance (including, but not limited to, other types of exercise equipment) having a display monitor/screen). During use (e.g., during a workout), the biometric connector sensor(s) detect biometric data for a user performing the workout, optionally store the biometric data locally (within the biometric connector sensor(s)), transform (e.g., via a microcontroller or processor thereof) the biometric data based on one or more algorithms to produce transformed biometric data (optionally having a non-numeric format, such as a graphical representation(s), sound(s) of varying intensity, color(s) of varying intensity, vibration(s) of varying intensity, or other sensory output(s)), and generate and transmit signals representing the transformed biometric data to the smart mirror (and/or an app running on the smart mirror, and/or a mobile compute device of the user) for presentation. The one or more algorithms can include one or more of: machine learning algorithms, statistical algorithms, unit conversion algorithms, biometric algorithms, encryption algorithms, and data compression algorithms. The transformed biometric data can include one or more of: compressed data, encrypted data, converted data, and modified data. Once received, one or more of the following actions can be performed: the transformed biometric data can be stored in memory, a representation of the transformed biometric data (e.g., in text, graphic, and/or audio form) can be presented to the user via the smart mirror and/or via the mobile compute device), an alert can be generated based on the transformed biometric data and presented to the user (e.g., in text, graphic, and/or audio form) via the smart mirror and/or via the mobile compute device, one or more recommendations (e.g., to correct form, to reduce intensity, to begin cool down, to increase intensity, to hydrate, to change to a different workout, etc.) can be generated based on the transformed biometric data (e.g., according to one or more predetermined rules and/or based on one or more algorithms) and presented to the user (e.g., in text, graphic, and/or audio form) via the smart mirror and/or via the mobile compute device), etc.

In some embodiments, a biometric connector system includes multiple biometric connector sensors, each configured to communicate (e.g., via Bluetooth® or other wireless network communications protocol) with one or more smart mirrors (and/or with any other wall-mounted or freestanding appliance (including, but not limited to, other types of exercise equipment) having a display monitor/screen). At least one biometric connector sensor from the multiple biometric connector sensors is attached to, embedded in, or otherwise associated with another type of exercise equipment, such as a treadmill, elliptical trainer, stationary bicycle, stair-stepper, rowing machine, cross-country ski machine, etc. The one or more smart mirrors (and/or an app running on the smart mirror(s), and/or mobile compute device(s) of the user(s)), upon receipt of biometric data from the other exercise equipment, may detect a type of exercise equipment associated with the biometric data, and select an algorithm and/or rule set for interpreting the biometric data based on the detected type of exercise equipment.

In addition to, or alternatively to, the sensors and detection techniques described herein, vibration, muscle activation, and other biometric data can be generated by one or more sensors and/or techniques described in U.S. Pat. No. 8,912,909, issued Dec. 16, 2014 and titled "Noninvasive Multi-Parameter Patient Monitor"; U.S. Patent Application Publication Number 2018/0271409, published Sep. 27, 2018 and titled "Body Part Motion Analysis with Wearable Sensors"; and U.S. Patent Application Publication Number 2019/0022388, published Jan. 24, 2019 and titled "Device and System to Measure and Assess Superficial Muscle Contractile Characteristics," the entire contents of each of which are herein incorporated by reference in their entireties for all purposes.

In some embodiments, biometric data is gathered, over time, from each of a plurality of networked smart mirrors (and/or from any other wall-mounted or freestanding appliance (including, but not limited to, other types of exercise equipment) having a display monitor/screen) and for each of a plurality of smart mirror users, and stored in a centralized repository (e.g., a cloud server). One or more machine learning models can be trained using the stored biometric data, to produce one or more trained machine learning models. The one or more trained machine learning models can detect, optionally adaptively over time (by retraining the one or more trained machine learning models based on additional biometric data gathered since the previous machine learning training), trends among subgroups of smart mirror users, such as: workout popularity, low performance statistics for individual workouts, high performance statistics for individual workouts, high interaction with other users during certain time periods, high interaction with other users during certain workouts, high interaction with other users on certain days, high interaction with other users for certain instructors, etc.

In some embodiments, biometric data is gathered, over time, from each of a plurality of networked smart mirrors (and/or from any other wall-mounted or freestanding appliance (including, but not limited to, other types of exercise equipment) having a display monitor/screen) and for each of a plurality of smart mirror users, and stored in a centralized repository (e.g., a cloud server). One or more machine learning models can be trained using a subset of the stored biometric data, the subset of the stored biometric data being selected based on one or more properties of a given user (e.g., biometric data, age, gender, height, weight, workout preferences, past workout performance, fitness level, etc.) to produce one or more trained machine learning models. The one or more trained machine learning models can then generate, optionally adaptively over time (by retraining the one or more trained machine learning models based on additional biometric data gathered since the previous machine learning training), recommendations for the user, including one or more of (but not limited to): recommended modifications to form (e.g., body positioning), workout recommendations, instructor recommendations, "friend" (i.e., other smart mirror user) recommendations, etc. The recommendations can also be based, in part, on one or more predefined user-customizable goals. For example, the trained machine learning model(s) can generate recommendations that are predicted to result in the user moving closer to his/her goal(s). Examples of user-customizable goals can include metrics such as (but not limited to): fitness level, mastery score (discussed further below), sport-specific fitness level (e.g., specific to yoga, running, calisthenics, cycling, biometric data (e.g., during the performance of one or more specified workouts), sport-specific form, sport-specific performance, workout-specific form, workout-specific performance, exercise-specific form, or exercise-specific performance. In some implementations, a first user can customize his/her goals by inputting (via a GUI of the smart mirror or mobile compute device) a name or identifier of one or more other smart mirror users, along with the metric(s) of that other smart mirror user that the first user would like to attain or progress toward.

In some embodiments, a biometric connector system includes one or more "connected weights." As used herein, a connected weight can refer to exercise equipment that (1) includes or is combined with one or more sensors, and (2) is configured to communicate with one or more smart mirrors and/or compute devices (e.g., to transmit/send sensor data generated by the one or more sensors). The communication can be via Bluetooth® or any other wireless network communications protocol. The one or more sensors (and, optionally, additional electronics such as a power supply, a transceiver, a transmitter, an antenna, a processor (e.g., a microprocessor), and/or a memory) can include one or more sensors positioned within the exercise equipment (e.g., within an external housing, coating (e.g., neoprene or rubber), or layer thereof), one or more sensors positioned on or around at least an exterior portion of the exercise equipment (e.g., mechanically clamped thereto, adhered thereto via an adhesive, secured thereto using a fastener such as a hook-and-loop fastener, engaged therewith via a screw-thread engagement, connected thereto via a friction fit fastener, etc.), and/or one or more sensors that are embedded in or formed integrally with the external housing, coating, or layer of the exercise equipment. The one or more sensors and optional electronics can be co-located within a housing or on a common substrate of the exercise equipment, and the sensors, optional electronics, and housing or substrate can collectively be referred to as a "connector sensor" (the term "connector" referring to the wireless communication connectivity established between the connected weight and the one or more smart mirrors and/or compute devices with which the connected weight can communicate). The connector sensor can have a form factor such that it is readily coupled to exercise equipment. For example, in some embodiments, a connector sensor includes a housing having an actuator (e.g., a spring-loaded button) and having an inner surface (e.g., a threaded inner surface). The housing is configured to mechanically couple, via the inner surface, to a complementary outer surface (e.g., a threaded outer surface) of a dumbbell. The complementary outer surface of the dumbbell can be positioned, for example, on a handle/bar of the dumbbell. The connector sensor also includes at least one power supply disposed within the housing, and at least one sensor, a processor, and a transceiver, each disposed within the housing and electrically coupled to the power supply. The processor is configured to receive a first signal representing signal data from the at least one sensor when the housing is mechanically coupled to the dumbbell, and to cause the transceiver to transmit a second signal representing the signal data to a smart mirror.

Exercise equipment can include any apparatus or device that can be used during physical activity to enhance the strength or conditioning effects of that physical activity. Examples of exercise equipment suitable for use as part of a connected weight include, but are not limited to, free weights such as dumbbells (e.g., hex head dumbbells, rubber dumbbells, urethane dumbbells, chrome dumbbells, spin-lock dumbbells, etc.), kettlebells, barbells, long bars, curl bars, angle weights, collars, tricep bars, hexagon-shaped bars, weight plates, cables and/or resistance bands.

In some embodiments, a connected weight includes a dumbbell, barbell, or other exercise equipment, and a connector sensor (e.g., sized and shaped as an easy-slide nut, discussed below) that is attached to the dumbbell, barbell, or other exercise equipment. The connector sensor includes one or more sensors. The one or more sensors include one or more of: a sensor configured to detect position and orientation (e.g., a gyroscope or magnetometer), a sensor configured to detect position (e.g., a GPS sensor or an altimeter), a sensor configured to detect orientation, a sensor configured to detect acceleration and velocity (e.g., an accelerometer, such as a 3-axis accelerometer), a sensor configured to detect acceleration, a sensor configured to detect speed/velocity, a sensor configured to detect cadence, a sensor configured to detect vibration, a sensor configured to detect muscle activation (e.g., a stretch sensor or a vibration sensor), a sensor configured to detect temperature, a sensor configured to detect humidity, a sensor configured to detect oxygen level(s) (e.g., blood oxygen level(s)), a sensor configured to detect blood oxygen saturation, a sensor configured to detect salinity, a sensor configured to detect breathing rate, a sensor configured to detect heart rate (e.g. a bioimpedance sensor, an optical sensor, a PPS sensor, etc.), or any other sensor described herein. The connector sensor also optionally includes one or more of: a power supply, a transceiver, a transmitter, an antenna, a processor (e.g., a microprocessor), or a memory. The connector sensor can include a housing within which the one or more sensors, the power supply, the transceiver, the transmitter, the antenna, the processor, or the memory are positioned.

In some embodiments, a connected weight includes a dumbbell or other exercise equipment and one or more sensors that are embedded within and contained within the exercise equipment. In addition to the one or more sensors, the connected weight also optionally includes, embedded therein or contained therewithin, one or more of: a power supply, a transceiver, a transmitter, an antenna, a processor (e.g., a microprocessor), or a memory.

Figure 6:
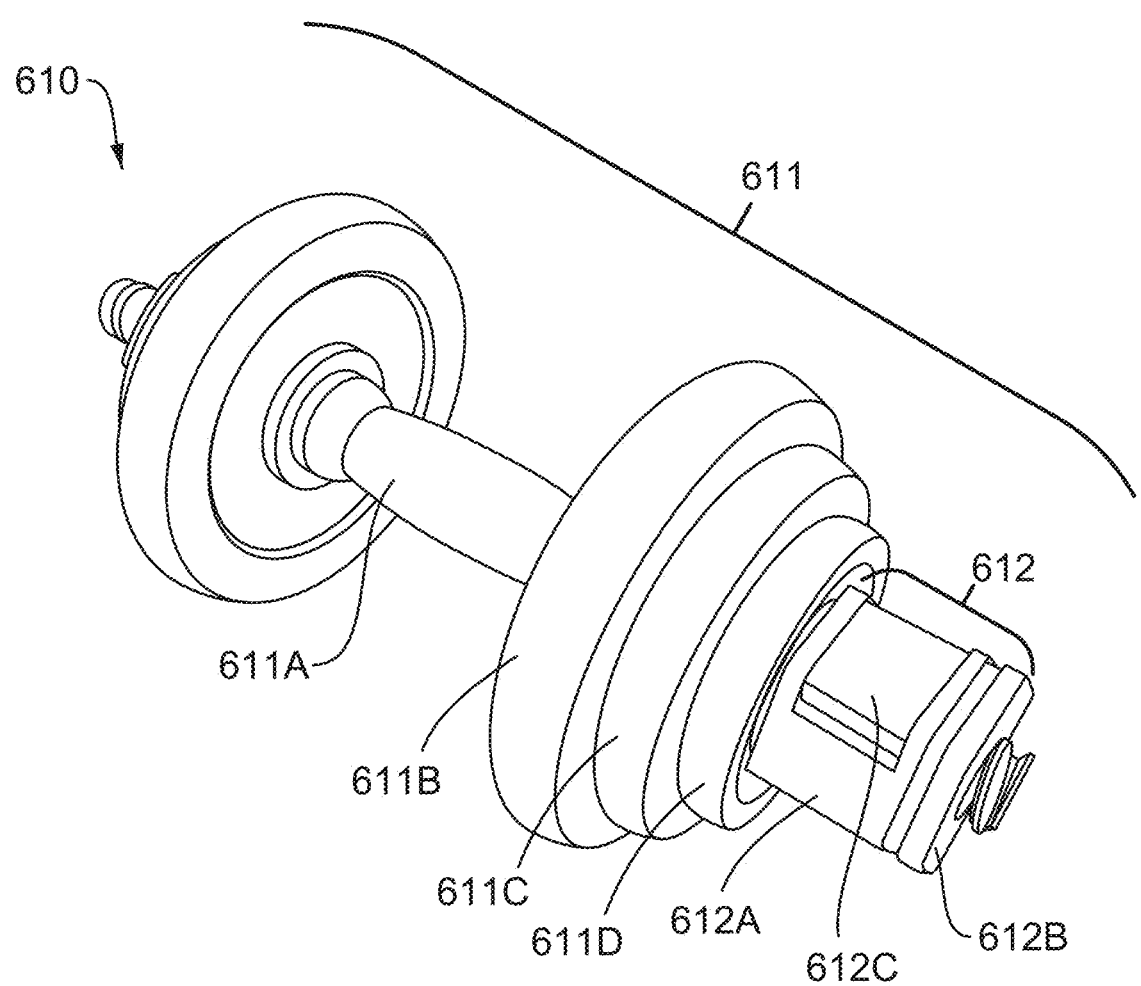
FIG. 6 is a rendering of a connected weight, including a dumbbell and a connector sensor, in accordance with some embodiments.
Figure 7:
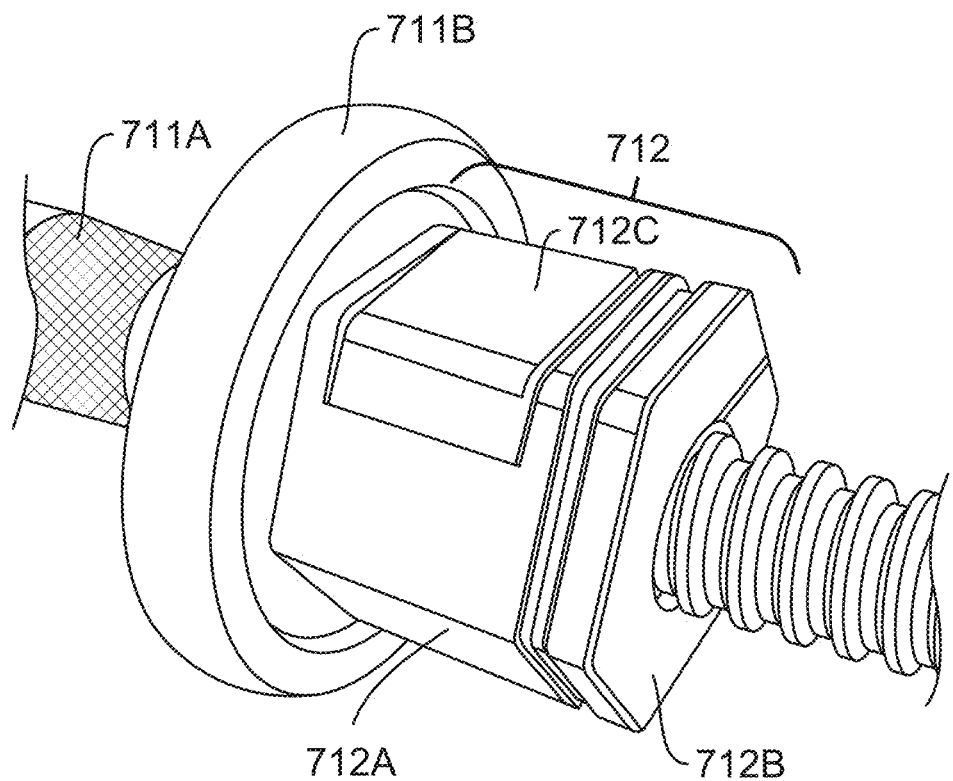
FIG. 7 is a photographic image of a connected weight, including a dumbbell and a connector sensor, in accordance with some embodiments.

In some embodiments, a connected weight includes a dumbbell and a connector sensor that is configured as an "easy-slide nut," as shown in FIGS. 6-7. For example, FIG. 6 is a rendering of a connected weight 610 including a dumbbell 611 and a connector sensor 612 configured as an easy-slide nut (or locking nut). The dumbbell 611 includes a handle or bar 611A and plurality of weighted plates 611B-611D. In some embodiments, the dumbbell 611 is an adjustable dumbbell, and during assembly of the connected weight 610, the weighted plates 611B-611D (i.e., a first set of weighted plates) are slid onto a first end of the handle/bar 611A, followed by the locking nut 612, which can be used to secure the weighted plates 611B-611D to the handle/bar 611A and prevent their movement along the handle/bar 611A during exercise. Also during assembly, a similar set of weighted plates (i.e., a second set of weighted plates) is slid onto a second end of the handle/bar 611A, the second end of the handle/bar 611A being opposite the first end of the handle/bar 611A. The second set of weighted plates may be secured by a non-functionalized nut or clamp (i.e., having no sensor or communication functionality) or by a second connector sensor (optionally also configured as a locking nut). During disassembly, the weighted plates 611B-611D can be removed from the handle/bar 611A by first removing the locking nut 612 from the handle/bar 611A and then sliding the weighted plates 611B-611D off the handle/bar 611A. In other embodiments, the dumbbell 611 is a non-adjustable dumbbell (i.e., including weighted plates that are integrally formed with, or otherwise permanently secured to, a handle/bar thereof), and a connector sensor is positioned at one or both ends thereof, for purposes of sensing but not to mechanically secure the weighted plates in place. In some such embodiments, a connector sensor is positioned at one end of the non-adjustable dumbbell and a non-functionalized nut or clamp at an opposite end of the non-adjustable dumbbell.

The locking nut connector sensor 612 includes a body portion 612A, an endcap portion 612B, and a spring-loaded button 612C. The body portion 612A and the endcap portion 612B may be distinct (e.g., separately formed) components that are configured to be mechanically coupled to one another (e.g., via press-fit, screw-thread engagement, etc.) or adhesively coupled to one another, or may be monolithically formed as a single component. In some embodiments, the locking nut connector sensor 612 includes a threaded internal surface configured to mechanically engage with a threaded surface of the handle/bar 611A. During installation of such a locking nut connector sensor 612 (e.g., after one or more of the weighted plates 611B-611D has been positioned on the handle/bar 611A), a user can depress the spring-loaded button 612C to cause the threads of the threaded internal surface of the locking nut connector sensor 612 to shift/move in an outward direction (e.g., radially away from a central longitudinal axis of the locking nut connector sensor 612). While the spring-loaded button 612C is depressed, the user can freely slide the locking nut connector sensor 612 along the handle/bar 611A to a desired position without the threaded internal surface of the locking nut connector sensor 612 engaging with the threaded surface of the handle/bar 611A. Once the user has positioned the locking nut connector sensor 612 at the desired position along the handle/bar 611A, the user can release the spring-loaded button 612C to cause the threads of the threaded internal surface of the locking nut connector sensor 612 to shift/move in an onward direction (e.g., radially toward the central longitudinal axis of the locking nut connector sensor 612) such that the threaded internal surface of the locking nut connector sensor 612 engages with the threaded surface of the handle/bar 611A. In some embodiments, the locking nut connector sensor 612, once engaged with the threaded surface of the handle/bar 611A, can be tightened about the handle/bar 611A (e.g., via manual rotation by the user) until a locked configuration is achieved. The locked configuration can refer to a desired amount of "tightness" (e.g., hand-tight), or can refer to configuration in which an amount of force between the threaded internal surface of the locking nut connector sensor 612 and the threaded surface of the handle/bar 611A. The locking nut connector sensor 612 can be configured to provide, during tightening, an indication (e.g., an audible or haptic click) that the locked configuration has been reached.

In some embodiments, the locking nut connector sensor 612 is configured to provide feedback to the user, for example in the form of an audible sound, a visible indication (such as a light or video display), and/or haptic feedback. When the feedback is audible or haptic, it can be through the same mechanism as in the locking nut connector sensor 612, or a different/distinct component. The feedback can be provided in response to detecting a condition, for example, that a form, movement, or action of the user when performing exercise is incorrect, undesirable, or dangerous (e.g., lifting movement is too fast, lowering movement is too fast, an incorrect grip on the connected weight 610, movement with the wrong positioning or trajectory, etc.). An undesirable form, movement, or action can be detected using one or more sensors (e.g., pressure sensors, accelerometers, etc.) and can be based on one or more predefined rules, which may include user-defined or user-reconfigurable rules. The detecting of the condition, the selection or generation of the feedback, and the providing of the feedback can be performed within the locking nut connector sensor 612 alone, within one or more smart mirror(s) that receive data from the locking nut connector sensor 612 alone, or within both the locking nut connector sensor 612 and the one or more smart mirror(s).

In some embodiments, a locking nut is non-functionalized (i.e., does not include any sensors or electronics), but functions mechanically in a manner similar to that described above. In other words, the non-functionalized locking nut can include a body portion, an endcap portion, and a spring-loaded button. The body portion and the endcap portion may be distinct (e.g., separately formed) components that are configured to be mechanically coupled to one another (e.g., via press-fit, screw-thread engagement, etc.) or adhesively coupled to one another, or may be monolithically formed as a single component. In some embodiments, the non-functionalized locking nut includes a threaded internal surface configured to mechanically engage with a threaded surface of a handle/bar. During installation of such a non-functionalized locking nut (e.g., after one or more weighted plates has been positioned on the handle/bar), a user can depress the spring-loaded button to cause the threads of the threaded internal surface of the non-functionalized locking nut to shift/move in an outward direction (e.g., radially away from a central longitudinal axis of the non-functionalized locking nut). While the spring-loaded button is depressed, the user can freely slide the non-functionalized locking nut along the handle/bar to a desired position without the threaded internal surface of the non-functionalized locking nut engaging with the threaded surface of the handle/bar. Once the user has positioned the non-functionalized locking nut at the desired position along the handle/bar, the user can release the spring-loaded button to cause the threads of the threaded internal surface of the non-functionalized locking nut to shift/move in an onward direction (e.g., radially toward the central longitudinal axis of the non-functionalized locking nut) such that the threaded internal surface of the non-functionalized locking nut engages with the threaded surface of the handle/bar. In some embodiments, the non-functionalized locking nut, once engaged with the threaded surface of the handle/bar, can be tightened about the handle/bar (e.g., via manual rotation by the user) until a locked configuration is achieved. The locked configuration can refer to a desired amount of "tightness" (e.g., hand-tight), or can refer to a configuration in which an amount of force between the threaded internal surface of the non-functionalized locking nut and the threaded surface of the handle/bar. The non-functionalized locking nut can be configured to provide, during tightening, an indication (e.g., an audible or haptic click) that the locked configuration has been reached.

FIG. 7 is a photographic image of a connected weight, including a dumbbell and a connector sensor, in accordance with some embodiments. As shown in FIG. 7, the connected weight dumbbell includes a handle/bar 711A and a single weighted plate 711B at a first end of the handle/bar 711A. The single weighted plate 711B is secured in place along the handle/bar 711A by a locking nut connector sensor 712 (similar to the locking nut connector sensor 612 of FIG. 6) having a body portion 712A, an endcap portion 712B, and a spring-loaded button 712C. Another single weighted plate (not shown) is positioned at a second end of the handle/bar 711A, the second end opposite the first end.

In some embodiments, a given connected weight of the present disclosure, such as the connected weight 610 of FIG. 6 or the connected weight dumbbell shown in FIG. 7, is configured (e.g., has a size and shape) to be removably connected to, and is compatible with, multiple different types of exercise equipment (e.g., weights made by different manufacturers and/or having different physical characteristics). In other words, existing exercise equipment can be retrofit to include functionalities described herein by attaching one or more of the locking nut connector sensors to the exercise equipment.

Figure 8:
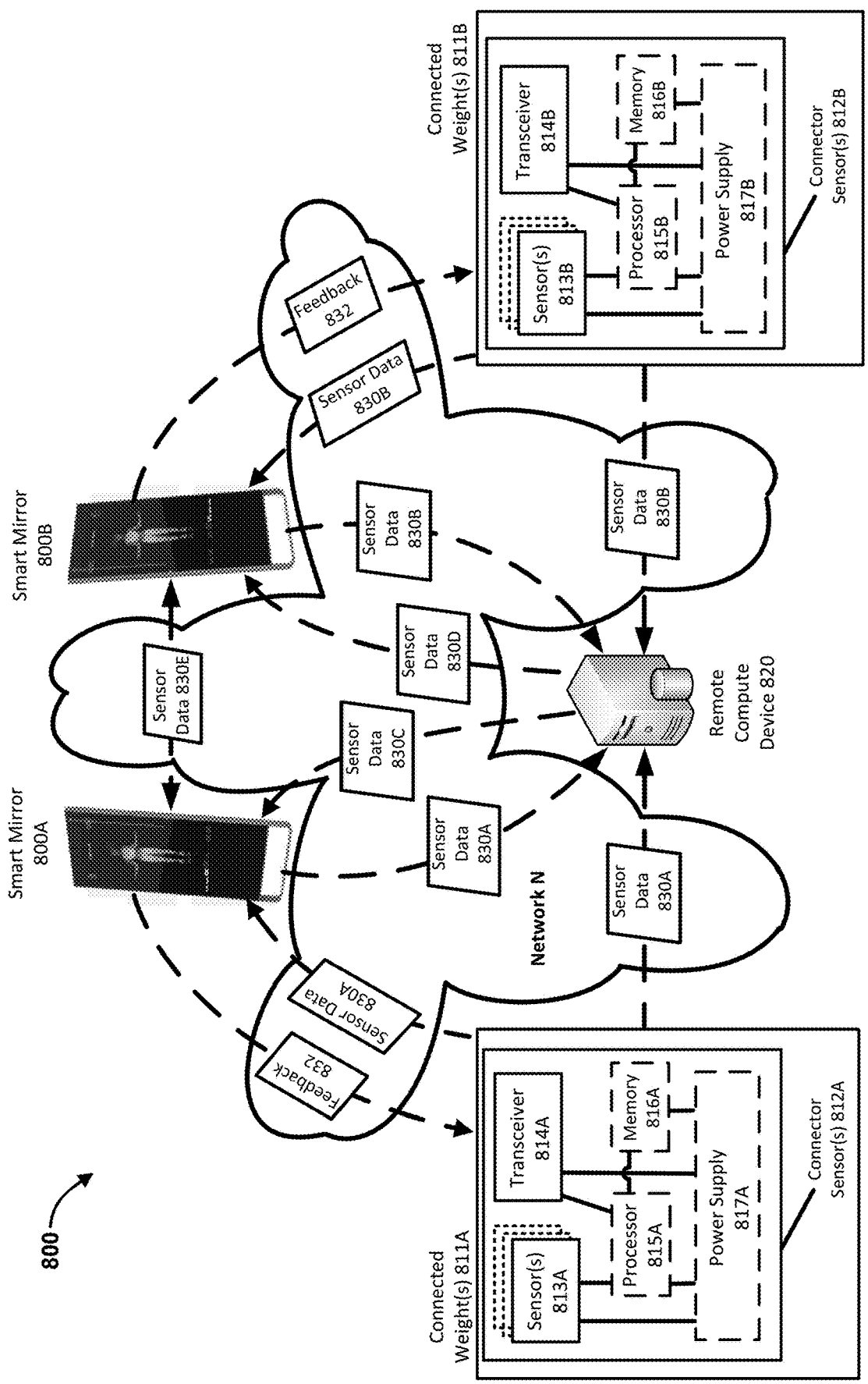
FIG. 8 is a system diagram showing connected weights and smart mirrors, in accordance with some embodiments.

FIG. 8 is a system diagram showing connected weights and smart mirrors, in accordance with some embodiments. As shown in FIG. 8, the system 800 includes a first connected weight 811A and a second connected weight 811B. The first connected weight 811A may be in close proximity (e.g., within about 10 feet) of a first smart mirror 800A and associated with a first user. The second connected weight 811B may be in close proximity (e.g., within about 10 feet) of a second smart mirror 800B and associated with a second user in a location different from a location of the first user. The first connected weight 811A includes one or more first connector sensors 812A each including one or more sensors 813A, a transceiver 814A, an optional processor 815A, an optional memory 816A, and an optional power supply 817A. Similarly, the second connected weight 811B includes one or more second connector sensors 812B each including one or more sensors 813B, a transceiver 814B, an optional processor 815B, an optional memory 816B, and an optional power supply 817B. In some implementations, one or more of the sensors 813A and/or one or more of the sensors 813B can include its own onboard power supply, processor, memory and/or transceiver, separate from the optional power supplies 817A, 817B, the optional processors 815A, 815B, the optional memories 816A, 816B, and the transceivers 814A, 814B. Each of the connected weights 811A, 811B can communicate (e.g., using the transceivers 812A and 812B, respectively) via a wireless communications network "N" with a remote compute device 820 and/or with the associated smart mirror (smart mirror 800A and smart mirror 800B, respectively), to send sensor data (830A and 830B, respectively) generated by the sensors 813A, 813B during exercise. As shown in FIG. 8, sensor data 830A can be sent from the connector sensor(s) 812A to the remote compute device 820 and/or to the smart mirror 800A. Similarly, sensor data 830B can be sent from the connector sensor(s) 812B to the remote compute device 820 and/or to the smart mirror 800B. Sensor data that is sent to the remote compute device 820 can be sent to the smart mirrors 800A, 800A. For example, sensor data 830C can include sensor data 830A, sensor data 830B, or both. Similarly, for example, sensor data 830D can include sensor data 830A, sensor data 830B, or both. The sensor data 830C and/or the sensor data 830D can include raw sensor data (i.e., data as received from the connected weight(s) 811A, 811B) and/or can include a modified version of the raw sensor data. For example, the sensor data 830C and/or the sensor data 830D can include normalized data, combined data, averaged data, etc. In some embodiments, the raw sensor data is modified based on an artificial intelligence ("AI") algorithm (e.g., a regression-based AI algorithm, such as linear regression, support vector regression ("SVR"), regression trees, neural network regression, decision trees, LASSO regression, ridge regression, ElasticNet regression, etc.) and a pattern-matching detection technique can be used to determine a movement of the user(s) and/or a quality of a performance of the user(s). Optionally, the first smart mirror 800A and the second smart mirror 800B are configured to communicate with one another directly, for example to exchange sensor data 830E about the first user and/or the second user.

Figure 9A:
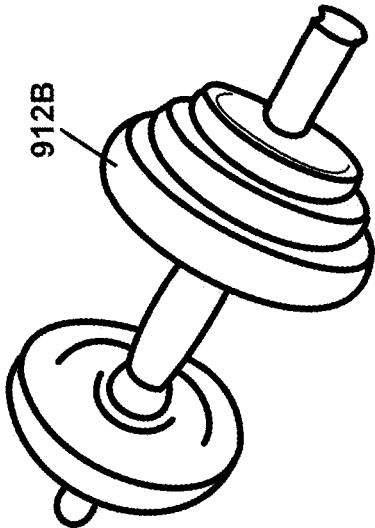
FIGS. 9A-9I are diagrams of example connected weight configurations, in accordance with some embodiments.
Figure 9B:
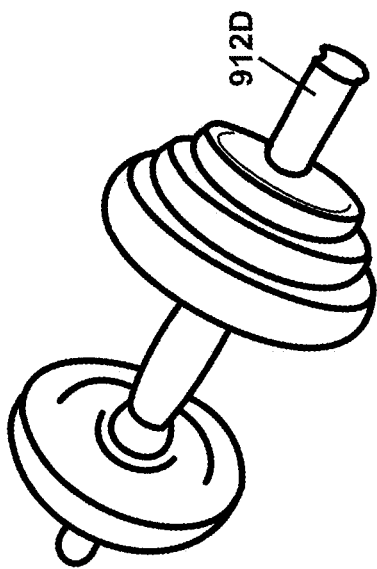
Figure 9C:
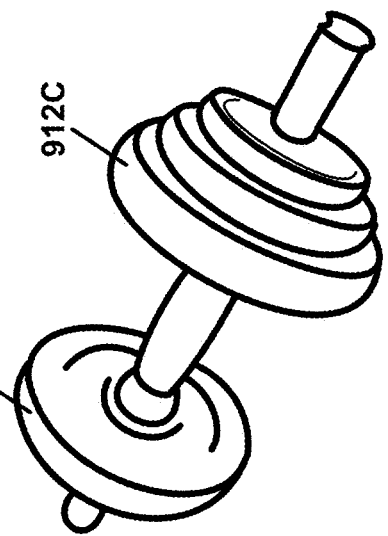
Figure 9D:

FIGS. 9A-9I are diagrams of example connected weight configurations, in accordance with some embodiments. FIG. 9A shows a connected weight including a dumbbell and a connector sensor 912A positioned on or within a grip disposed on the handle/bar of the dumbbell. FIG. 9B shows a connected weight including a dumbbell and a connector sensor 912B positioned on or within a weight plate of the dumbbell. FIG. 9C shows a connected weight including a dumbbell and connector sensors 912C positioned on or within multiple weight plates of the dumbbell. FIG. 9D shows a connected weight including a dumbbell and a connector sensor 912D positioned on or within one handle/bar of the dumbbell. In some such embodiments, the connector sensor 912D is positioned on a first handle of the dumbbell, and a "dumb" locking nut (i.e., a locking nut that does not include sensors, and thus is not "smart," but still functions to secure a weight plate of the connected weight along the second handle) is positioned on a second handle of the dumbbell, the second handle opposite the first handle. The dumb locking nut may have substantially the same external appearance as the connector sensor 912D, and/or may weigh substantially the same as the connector sensor 912D.

Figure 9H:
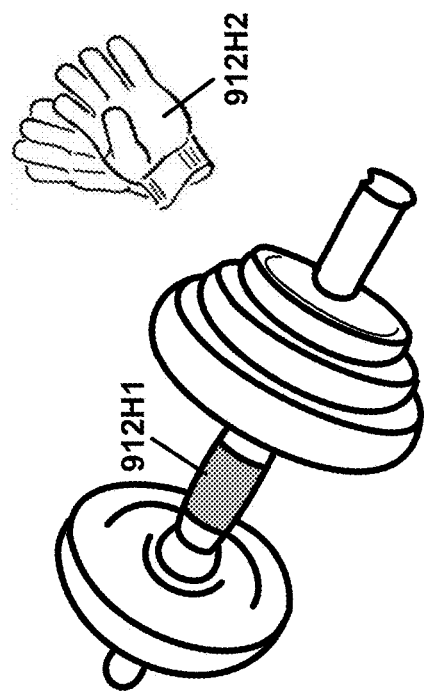
Figure 9F:
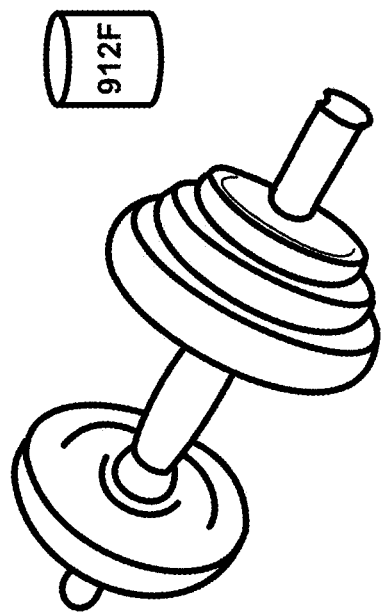
Figure 9G:
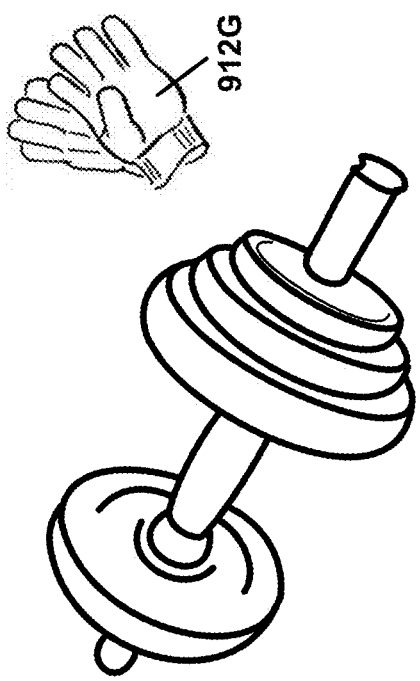
Figure 9E:
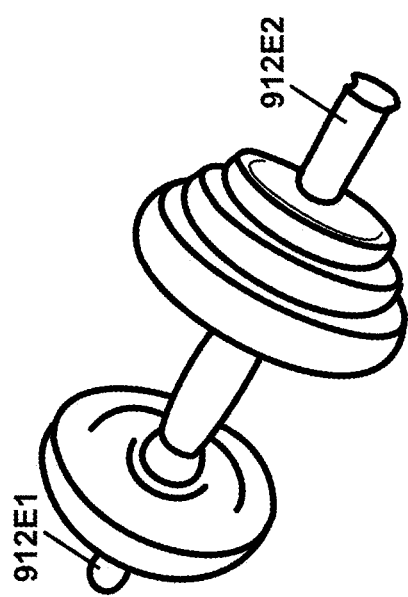

FIG. 9E shows a connected weight including a dumbbell and connector sensors 912E1, 912E2 positioned on or within both ends of the handle/bar of the dumbbell. FIG. 9F shows a connected weight including a dumbbell and a separate connector sensor 912F positioned in close proximity to (e.g., within 10 feet or within 5 feet of) the dumbbell, for example on the user's body, clothing, or shoes. The separate connector sensor 912F may include a camera configured to detect and optionally analyze a user's movements. FIG. 9G shows a connected weight including a dumbbell and a connector sensor comprising a glove accessory 912G positioned in close proximity to (e.g., within 10 feet or within 5 feet of) the dumbbell. FIG. 9H shows a connected weight including a dumbbell with a first connector sensor 912H1 and a second connector sensor comprising a glove accessory 912H2 positioned in close proximity to (e.g., within 10 feet or within 5 feet of) the dumbbell. During exercise, a user wears the glove accessory 912H2, and when gripping the dumbbell, an active portion of the glove accessory 912H2 contacts the first connector sensor 912H1, for example such that biometric sensor data detected by the glove accessory can be transferred from the glove accessory to the first connector sensor 912H1.

Figure 9I:
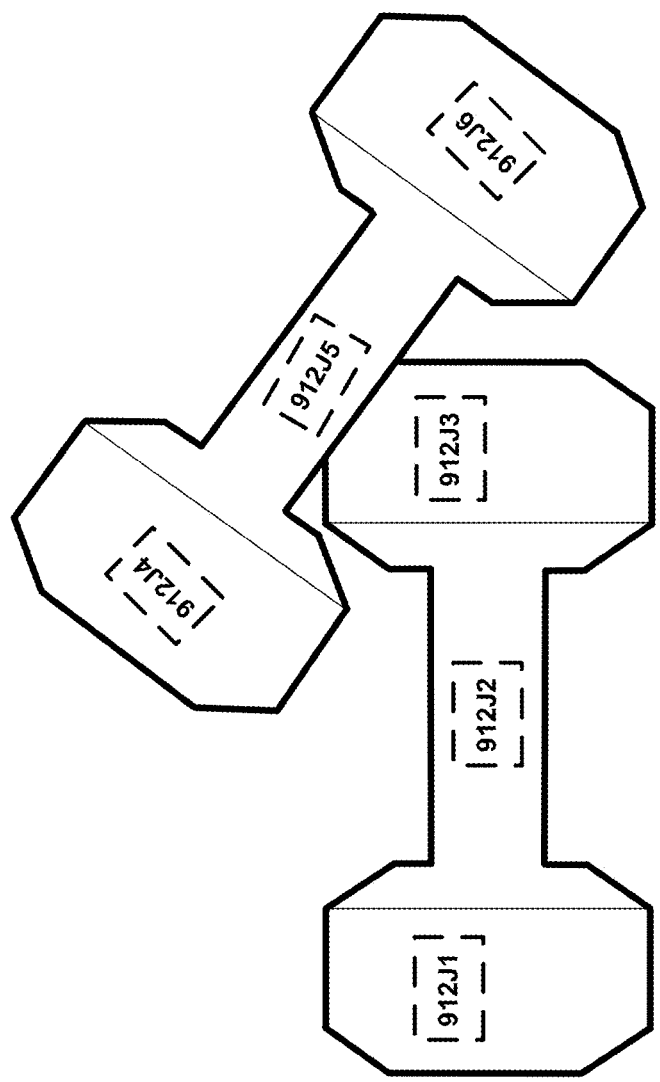

FIG. 9I shows a pair of dumbbells, one or both of which can be a connected weight. As shown in FIG. 9I, a first dumbbell from the pair of dumbbells can include a connector sensor 912J1 and/or a connector sensor 912J2. Similarly, a second dumbbell from the pair of dumbbells can include a connector sensor 912J3 and/or a connector sensor 912J4. Each of the optional connector sensors 912J1, 912J2, 912J3, and 912J4 can be embedded within or contained within the dumbbell(s), within the bar region and/or the "head" region(s) thereof.

During use by a user (e.g., during exercise) of any of the connected weights shown in FIGS. 9A-9I, real-time data (e.g., similar to sensor data 830A, 830B of FIG. 8), including raw data and/or modified data, can be transmitted from the connected weight(s) to one or more smart mirrors and/or remote compute devices (e.g., mobile devices such as smart phones) in communication (e.g., wireless network communication) with the connected weight(s). The real-time data can include, for example, repetition count(s), movement data (e.g., speed, velocity, direction, acceleration, position data, etc.). In response to, and based on, the real-time data, the one or more smart mirrors and/or the one or more remote compute devices can generate one or more messages for display to the user via the smart mirror(s) and/or the remote compute device(s). The one or more messages can include a text, graphic, video and/or audio representation of one or more of: repetition count(s), recommended weight modifications (e.g., a recommendation that the user use heavier weight(s) or lighter weight(s), which may or may not be connected weight(s)), or recommended form modifications (e.g., a recommendation that the user modify the way that the user is holding/gripping the connected weight(s), or a recommendation that the user modify a body positioning or stance). Generating the one or more messages can include the use of one or more AI algorithms. In some embodiments, the one or more smart mirrors and/or the one or more remote compute devices can use the real-time data to perform comparisons of users (thereby generating comparison data), and the one or more messages can include a representation of the comparison data or a representation of a user's relative performance as compared to one or more other specified users.

Biometric Connector Software

In some embodiments, a biometric connector system includes a connector software application having instructions to cause a processor to calculate a mastery score (or "fluidity score") according to an algorithm. In one example, the mastery score is calculated based on a number of repetitions completed, one or more movement patterns, body positioning data (e.g., including coordinates within three-dimensional space and representations of associated body parts), muscle usage/activation data, cadence, and heart rate recovery data for a given user. In some such implementations, the algorithm combines calculated values (e.g., calculated based on data from one or more sensors) with raw sensor data to determine the mastery score. Once calculated, the mastery score can be presented to the user (e.g., in text, graphic, and/or audio form) via the smart mirror and/or via the mobile compute device of the user. The data from one or more sensors, the calculated values, and/or the raw sensor data can include data generated by and/or received from one or more connected weights (such as connected weight 610 of FIG. 6).

In some embodiments, a biometric connector system includes a connector software application having instructions to cause a processor to capture video of a user completing exercises, during a first workout period, and stores that video as a first archive video (optionally associated, in memory, with one or more of: a timestamp, date stamp, and biometric data). During a second workout period subsequent to the first workout period, the connector software application can be configured to cause display, via the smart mirror, of an overlay of the first archive video, optionally in combination with the biometric data of the first archive video, such that the user can see his/her reflected image concurrently with the first archive video of himself/herself (e.g., for self-comparison, competition with one's own prior performance, etc.). In some embodiments, the overlay can include a visual representation of data collected via one or more connected weights during recording of the first archive video and/or one or more messages previously presented to a user during the recording of the first archive video and based on data generated by one or more connected weights at that time. The overlay can include a visual representation of a form correction, an incorrect form/movement, and/or one or more muscles that are expected to be activated during a given exercise depicted in the first archive video.

In some embodiments, a biometric connector system includes a connector software application having instructions to cause a processor to combine video camera data/imagery captured by a smart mirror of a user with biometric data generated based on one or more wearable electronic accessories of the user (optionally synchronized in time or matched based on time of capture/generation) to define composite data, and make determinations based on the composite data or based on the video camera data/imagery and the biometric data sequentially. For example, a movement (e.g., a vibration, shaking, contraction, etc.) of the user can be detected based on the video camera data/imagery, and biometric data (e.g., generated by a vibration sensor, stretch sensor and/or other sensor) can be used to confirm the movement and/or specify which muscle(s) are most exhibiting the movement, relative to other muscles of the user. Alternatively, the movement of the user can be detected based on the biometric data, and the video camera data/imagery can be used to confirm the movement and/or specify which muscle(s) are most exhibiting the movement, relative to other muscles of the user. In some such embodiments, the video camera data/imagery, the biometric data, and/or the composite data can be compared to one or more expected values associated with a workout being performed by the user, via the smart mirror, concurrently with the capture of the video camera data/imagery and the generation of the biometric data. Based on the comparison, the connector software application may determine whether a given exercise is (or was) being properly performed by the user, and/or to assess a form or other performance of the user. Optionally, the determination as to whether a given exercise is (or was) being properly performed by the user, and/or to assess a form or other performance of the user can be further based on audio data generated by one or more microphones of the smart mirror.

Figure 5:
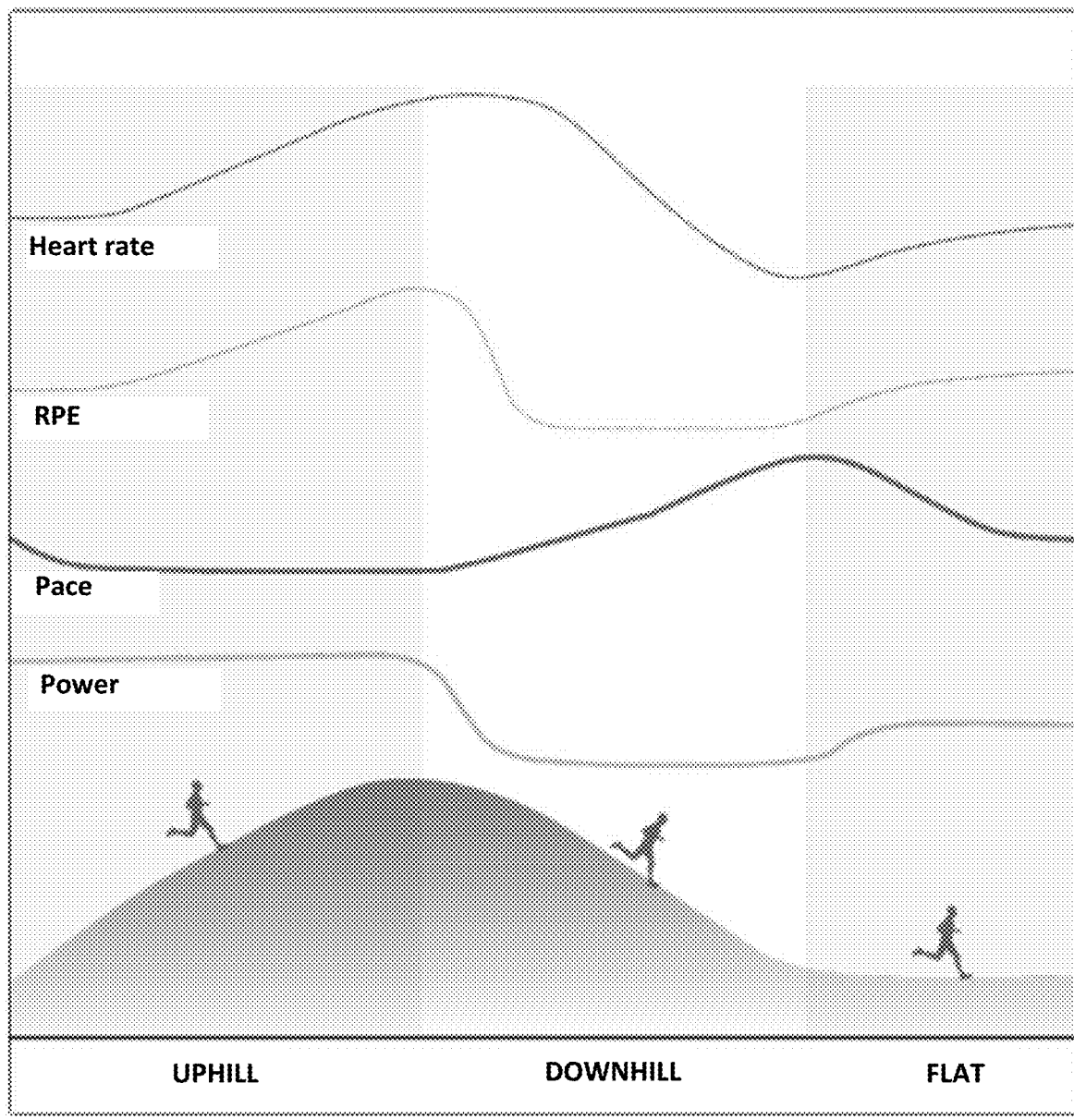
FIG. 5 is a diagram showing interrelatedness of certain biometric data parameters.

In some embodiments, optionally in combination with any of the preceding embodiments, biometric data can be used by the connector software application to calculate or infer a power (e.g., a running power) of a user during a workout. As used herein, "power" can refer to a user's ability to move weight with speed (also referred to as "explosiveness"). Power can be calculated, for example, using one or more techniques described in U.S. Pat. No. 10,744,371, issued Aug. 18, 2020 and titled "Methods and Apparatus for Power Expenditure and Technique Determination During Bipedal Motion," and in U.S. Patent Application Publication Number 2017/0189752, published Jul. 6, 2017 and titled "Methods and Apparatus for Power Expenditure and Technique Determination During Bipedal Motion," the entire contents of each of which are herein incorporated by reference in their entireties for all purposes. The connector software application can compare calculated power for a given time period and for a given user, with at least one other biometric data parameter, to confirm accuracy and/or to generate a more complete statistical profile of the user's performance during a given workout, sport, exercise, etc., which can be tracked over time. FIG. 5 is a diagram showing an example of interrelatedness of certain biometric data parameters (namely, heart rate, rate of perceived exertion (RPE), pace, and power) for a user running uphill, downhill, and on flat terrain. As an example, referring to FIG. 5, in some embodiments, the connector software application can compare calculated power for a first time period, during which a user is running uphill and then transitions to running downhill, with a heart rate, pace, and/or RPE of the user for the same time period, to confirm that the measurements of the associated sensors are accurate. As shown in FIG. 5, if the sensors are performing correctly, the heart rate and RPE (for the first time period) should increase, plateau, and then decrease; the pace should increase when the user is running downhill, relative to when the user was running uphill; and the power should decrease when the user is running downhill, relative to when the user was running uphill (e.g., at a faster rate than the decrease(s) of RPE and/or heart rate during the downhill segment of the run).

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Some embodiments and/or methods described herein can be performed by software (executed on hardware), hardware, or a combination thereof. Hardware modules may include, for example, a processor, a field programmable gate array (FPGA), and/or an application specific integrated circuit (ASIC). Software modules (executed on hardware) can include instructions stored in a memory that is operably coupled to a processor, and can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system, comprising:
a processor; and
a memory operably coupled to the processor and storing instructions that, when executed by the processor, cause the processor to:
host a workout session including (1) presentation of a workout video during a first time period, and (2) presentation of a simulated locker room during a second time period following the first time period and mutually exclusive of the first time period, the hosting including:
causing display, during the first time period and via each compute device from a first subset of at least two compute devices from a networked plurality of compute devices, of (1) a workout video including a depiction of a workout instructor, and (2) a representation of at least one user from a first plurality of users associated with the first subset of compute devices; and
causing display, during the second time period and via each compute device from a second subset of at least two compute devices from the networked plurality of compute devices, of live video depicting at least one user from a second plurality of users associated with the second subset of compute devices and without displaying a workout video including a depiction of a workout instructor.

2. The system of claim 1, wherein the first subset of compute devices and the second subset of compute devices have at least one compute device in common.

3. The system of claim 1, wherein each of the first subset of compute devices and the second subset of compute devices includes at least one smart mirror and at least one mobile communication device.

4. The system of claim 1, wherein the first subset of compute devices is configured such that users from the first plurality of users can communicate with one another during the first time period via at least one of: voice, video, text, emojis, animation, or imagery.

5. The system of claim 1, wherein the memory further stores instructions that, when executed by the processor, cause the processor to cause display, during the first time period and via each compute device from the first subset of compute devices from the networked plurality of compute devices, of at least one user-selected background.

6. The system of claim 5, wherein the at least one user-selected background includes a depiction of at least one product for promotion.

7. The system of claim 1, wherein the memory further stores instructions that, when executed by the processor, cause the processor to cause display, during the first time period and via each compute device from the first subset of compute devices from the networked plurality of compute devices, of at least one background, the at least one background automatically selected by a software application associated with the first subset of compute devices.

8. The system of claim 7, wherein the at least one background includes a depiction of an interior of a locker room.

9. The system of claim 1, wherein the memory further stores instructions that, when executed by the processor, cause the processor to modify an appearance of the live video during the first time period, in response to detecting that one of the users from the first plurality of users is speaking.

10. The system of claim 1, wherein the first plurality of users and the second plurality of users have at least one user in common.

11. A non-transitory, processor-readable medium storing processor-executable instructions to:
- host a workout session including (1) presentation of a workout video during a first time period, and (2) presentation of a simulated locker room during a second time period following the first time period and mutually exclusive of the first time period, the hosting including:
  - causing display, during the first time period and via each compute device from a first subset of at least two compute devices from a networked plurality of compute devices, of (1) a workout video including a depiction of a workout instructor, and (2) a representation of at least one user from a first plurality of users associated with the first subset of compute devices; and
  - causing display, during the second time period and via each compute device from a second subset of at least two compute devices from the networked plurality of compute devices, of live video depicting at least one user from a second plurality of users associated with the second subset of compute devices and without displaying a workout video including a depiction of a workout instructor.

12. The non-transitory, processor-readable medium of claim 11, wherein the first subset of compute devices and the second subset of compute devices have at least one compute device in common.

13. The non-transitory, processor-readable medium of claim 11, wherein each of the first subset of compute devices and the second subset of compute devices includes at least one smart mirror and at least one mobile communication device.

14. The non-transitory, processor-readable medium of claim 11, wherein the first subset of compute devices is configured such that users from the first plurality of users can communicate with one another during the first time period via at least one of: voice, video, text, emojis, animation, or imagery.

15. The non-transitory, processor-readable medium of claim 11, further storing instructions that, when executed by the processor, cause the processor to cause display, during the first time period and via each compute device from the first subset of compute devices from the networked plurality of compute devices, of at least one user-selected background.

16. The non-transitory, processor-readable medium of claim 15, wherein the at least one user-selected background includes a depiction of at least one product for promotion.

17. The non-transitory, processor-readable medium of claim 11, further storing instructions that, when executed by the processor, cause the processor to cause display, during the first time period and via each compute device from the first subset of compute devices from the networked plurality of compute devices, of at least one background, the at least one background automatically selected by a software application associated with the first subset of compute devices.

18. The non-transitory, processor-readable medium of claim 17, wherein the at least one background includes a depiction of an interior of a locker room.

19. The non-transitory, processor-readable medium of claim 11, further storing instructions that, when executed by the processor, cause the processor to modify an appearance of the live video during the first time period, in response to detecting that one of the users from the first plurality of users is speaking.

20. The non-transitory, processor-readable medium of claim 11, wherein the first plurality of users and the second plurality of users have at least one user in common.

* * * * *